United States Patent
Rousso et al.

(10) Patent No.: US 11,944,408 B1
(45) Date of Patent: Apr. 2, 2024

(54) METHOD AND SYSTEM FOR IMAGING A TISSUE USING ACOUSTO-ELECTRIC EFFECT

(71) Applicant: MDSG Innovation Ltd., Rehovot (IL)

(72) Inventors: Benny Rousso, Rishon-LeZion (IL); Assaf Erell, Rehovot (IL); Lior Eshel, Rishon-LeZion (IL); Naama Winetraub, Holon (IL); Boaz Rippin, Beit Yehoshua (IL)

(73) Assignee: MDSG Innovation Ltd., Rehovot (IL)

( * ) Notice: Subject to any disclaimer, the term of this patent is extended or adjusted under 35 U.S.C. 154(b) by 1053 days.

(21) Appl. No.: 16/170,244

(22) Filed: Oct. 25, 2018

Related U.S. Application Data

(60) Provisional application No. 62/576,775, filed on Oct. 25, 2017.

(51) Int. Cl.
*A61B 5/00* (2006.01)
*A61B 18/00* (2006.01)
*A61B 18/14* (2006.01)
*A61B 34/10* (2016.01)
*A61B 90/00* (2016.01)

(52) U.S. Cl.
CPC ........ *A61B 5/0093* (2013.01); *A61B 18/1492* (2013.01); *A61B 34/10* (2016.02); *A61B 2018/00351* (2013.01); *A61B 2018/00577* (2013.01); *A61B 2018/00904* (2013.01); *A61B 2034/105* (2016.02); *A61B 2090/367* (2016.02)

(58) Field of Classification Search
CPC ....... A61B 5/4064; A61B 5/4094; A61B 5/24; A61B 5/0093
See application file for complete search history.

(56) References Cited

U.S. PATENT DOCUMENTS

| | | |
|---|---|---|
| 6,520,911 B1 | 2/2003 | Wen |
| 6,645,144 B1 | 11/2003 | Wen et al. |
| 8,057,390 B2 | 11/2011 | Witte et al. |
| 8,427,906 B2 | 4/2013 | Witte et al. |
| 2002/0129655 A1 | 9/2002 | Diebold |
| 2004/0059234 A1* | 3/2004 | Martin ............... A61B 5/024 600/500 |

(Continued)

OTHER PUBLICATIONS

Kiymik ["Ultrasound imaging based on multiple beamforming with coded excitation", Signal Processing 58 (1997) 107-I 13 ]. (Year: 1997).*

(Continued)

*Primary Examiner* — Oommen Jacob

(57) ABSTRACT

An aspect of some embodiments of the invention relate to a system for tissue characterization using an acousto-electric effect comprising: at least one ultrasonic waveform generator; at least one waveform generation controller; at least one set of electrodes; at least one electric signal amplification circuitry connectable to at least one of said at least one set of electrodes to generate an amplified signal; and at least one signal processing unit for analyzing said amplified signal and to generate information related to properties of multiple locations within a target tissue; wherein at least one of said multiple location has no direct contact with any electrode, and wherein said properties of said multiple locations are obtained within up to 10 milliseconds per location on average.

22 Claims, 21 Drawing Sheets

(56) References Cited

U.S. PATENT DOCUMENTS

| | | | | |
|---|---|---|---|---|
| 2008/0183076 | A1* | 7/2008 | Witte | A61B 5/4064 600/438 |
| 2014/0031684 | A1* | 1/2014 | Troyansky | A61B 8/0808 600/437 |

OTHER PUBLICATIONS

Theyab ["Stanford Exploration Project", Report No. 136, Oct. 2008 ]. (Year: 2008).*

Ammari et al. "Mathematical Models and Reconstruction Methods in Magneto-Acoustic Imaging", European Journal of Applied Mathematics, 20(3): 303-317, Published Online Jun. 1, 2009.

Avitall et al. "The Effects of Electrode-Tissue Contact on Radiofrequency Lesion Generation", Pacing and Clinical Electrophysiology, PACE, 20(Pt.1): 2899-2910, Dec. 1997.

Delacretaz et al. "Assessment of Radiofrequency Ablation Effect From Unipolar Pacing Threshold", Pacing and Clinical Electrophysiology, PACE, 26(10): 1993-1996, Oct. 2003.

Dumas III et al. "Myocardial Electrical Impedance as A Predictor of the Quality of RF-Induced Linear Lesions", Physiological Measurement, 29(10): 1195-1207, Published Online Sep. 18, 2008.

Ganesan et al. "Long-Term Outcomes of Catheter Ablation of Atrial Fibrillation: A Systemic Review and Meta-Analysis", Journal of the American Heart Association, 2(2): e004549-1-e004549-14, Published Online Apr. 24, 2013.

Grasland-Mongrain et al. "Lorentz Force Electrical Impedance Tomography", Innovation and Research in Biomedical Engineering, 34(4-5): 357-360, Available Online Oct. 8, 2013.

Guan et al. "Towards A-Scan Imaging Via Ultrasonic Vibration Potential Measurements", Nuclear Engineering and Design, 241(6): 1994-1997, Jun. 2011.

Haines et al. "Near-Field Ultrasound Imaging During Radiofrequency Catheter Ablation: Tissue Thickness and Epicardial Wall Visualization and Assessment of Radiofrequency Ablation Lesion Formation and Depth", Circulation: Arrhythmia and Electrophysiology, 10(12): e005295-1-e005295-12, Dec. 2017.

Harvey et al. "Impedance Monitoring During Radiofrequency Catheter Ablation in Humans", Pacing and Clinical Electrophysiology, PACE, 15(1): Jan. 22-, 1992.

Hosseini et al. "An Experiment Investigation of Ionic Vibration Potential Sensing in Electrolytes", The 7th World Congress on Particle Technology, WCPT7, Procedia Engineering, 102: 64-71, Jan. 2015.

Hu et al. "Magnetoacoustic Imaging of Electrical Conductivity of Biological Tissues at A Spatial Resolution Better Than 2 MM", PLoS ONE, 6(8): e23421-1-e23421-9, Published Online Aug. 12, 2011.

Ikeda et al. "Relationship Between Catheter Contact Force and Radiofrequency Lesion Size and Incidence of Steam Pop in the Beating Canine Heart. Electrogram Amplitude, Impedance, and Electrode Temperature Are Poor Predictors of Electrode-Tissue Contact Force and Lesion Size", Circulation: Arrhythmia and Electrophysiology, 7(6): 1174-1180, Published Online Nov. 7, 2014.

Jossinet et al. "The Phenomenology of Acousto-Electric Interaction Signals in Aqueous Solutions of Electrolytes", Ultrasonics, 36(1-5): 607-613, Feb. 1998.

Kolandaivelu et al. "Noninvasive Assessment of Tissue Heating During Cardiac Radiofrequency Ablation Using MRI Thermography", Circulation: Arrhythmia and Electrophysiology, 3(5): 521-529, Oct. 2010.

Kubanek et al. "Ultrasound Modulates Ion Channel Currents", Scientific Reports, 6: 24170-1-24170-14, Published Online Apr. 26, 2016.

Kumar et al. "Better Lesion Creation and Assessment During Catheter Ablation", Journal of Atrial Fibrillation, 81(3): 62-73, Oct.-Nov. 2015.

Lavandier et al. "Experimental Measurement of the Acousto-Electric Interaction Signal in Saline Solution", Ultrasonics, 38(9): 929-936, Sep. 2000.

Li et al. "Measuring the Acoustoelectric Interaction Constant Using Ultrasound Current Source Density Imaging", Physics in Medicine and Biology, 57(19): 5929-5941, Published Online Sep. 7, 2012.

Li et al. "Ultrasound Current Source Density Imaging Using A Clinical Intracardiac Catheter", 2011 IEEE International Ultrasonics Symposium Proceedings, Orlando, Florida, USA, Oct. 18-21, 2011, p. 704-707, Oct. 18, 2011.

Martin et al. "First Clinical Use of Novel Ablation Catheter Incorporating Local Impedance Data", Journal of Cardiovascular Electrophysiology, 29(9): 1197-1206, Published Online Jun. 19, 2018.

Montalibet et al. "Electric Current Generated by Ultrasonically Induced Lorentz Force in Biological Media", Medical & Biological Engineering & Computing, 39(1): Jan. 15-20, 2001.

Montalibet et al. "Scanning Electric Conductivity Gradients With Ultrasonically-Induced Lorentz Force", Ultrasonic Imaging, 23(2): 117-132, Apr. 2001.

Olafsson et al. "Ultrasound Current Source Density Imaging", IEEE Transactions on Bio-Medical Engineering, 55(7): 1840-1848, Jul. 2008.

Qin et al. "Mapping the ECG in the Live Rabbit Heart Using Ultrasound Current Source Density Imaging With Coded Excitation", 2012 IEEE International Ultrasonics Symposium Proceedings, Dresden, Germany, Oct. 7-10, 2012, p. 910-913, Oct. 7, 2012.

Qin et al. "Ultrasound Current Source Density Imaging of the Cardiac Activation Wave Using A Clinical Cardiac Catheter", IEEE Transactions on Biomedical Engineering, 62(1): 241-247, Published Online Aug. 7, 2014.

Ranjan et al. "Gaps in the Ablation Line as A Potential Cause of Recovery From Electrical Isolation and Their Visualization Using MRI", Circulation: Arrhythmia and Electrophysiology, XP055452459, 4(3): 279-286, Published Online Apr. 14, 2011.

Ranjan et al. "Identification and Acute Targeting of Gaps in Atrial Ablation Lesions Sets Using A Real Time MRI System", Circulation: Arrhythmia and Electrophysiology, 5(6): 1130-1135, Dec. 2012.

Sapp et al. "Ablation Lesion Size Correlates With Pacing Threshold: A Physiological Basis for Use of Pacing to Assess Ablation Lesions", Pacing and Clinical Electrophysiology, PACE, 27(7): 933-937, Jul. 2004.

Spector et al. "Meta-Analysis of Ablation of Atrial Flutter and Supraventricular Tachycardia", The American Journal of Cardiology, 104(5): 671-677, Sep. 2009.

Stagegaard et al. "Indication of the Radiofrequency Induced Lesion Size by Pre-Ablation Measurements", Europace, 7(6): 525-534, Available Online Sep. 8, 2005.

Stevenson et al. "Irrigated Radiofrequency Catheter Ablation Guided by Electroanatomic Mapping for Recurrent Ventricular Tachycardia After Myocardial Infarction: The Multicenter Thermocool Ventricular Tachycardia Ablation Trial", Circulation, 118(25): 2773-2782, Published Online Dec. 8, 2008.

Thiagalingam et al. "Importance of Catheter Contact Force During Irrigated Radiofrequency Ablation: Evaluation in A Porcine Ex Vivo Model Using A Force-Sensing Catheter", Journal of Cardiovascular Electrophysiology, 21(7): 806-811, Jul. 2010.

Wang et al. "Detection of Multiple Electrical Sources in Tissue Using Ultrasound Current Source Density Imaging", Medical Imaging 2010: Ultrasonic Imaging, Tomography, and Therapy, Proceedings of the SPIE, 7629: 76290H-1-76290H—, Mar. 12, 2010.

Wang et al. "Multichannel Ultrasound Current Source Density Imaging of A 3-D Dipole Field", 2010 IEEE International Ultrasonics Symposium, San Diego, CA, USA, Oct. 11-14, 2010, p. 253-256, Oct. 11, 2010.

Wang et al. "Simulation-Based Validation for Four-Dimensional Multi-Channel Ultrasound Current Source Density Imaging", IEEE Transactions on Ultrasonics, Ferroelectrics and Frequency Control, 61(3): 420-427, Mar. 2014.

Warren et al. "Percutaneous Electrocatheter Technique for On-Line Detection of Healed Transmural Myocardial Infarction", Pacing and Clinical Electrophysiology, PACE, 23(8): 1283-1287, Aug. 2000.

(56) References Cited

OTHER PUBLICATIONS

Wen et al. "Hall Effect Imaging", IEEE Transactions on Bio-Medical Engineering, 45(1): 119-124, Jan. 1998.

Wen et al. "Ultrasonic Imaging of the Electroacoustic Effect in Macromolecular Gels", Ultrasonic Imaging, 20(4): 288-297, Oct. 1998.

Wolf et al. "Three-Dimensional Endocardial Impedance Mapping: A New Approach for Myocardial Infarction Assessment", American Journal of Heart Circulation and Physiology, 28091): H179-H188, Jan. 2001.

Yokoyama et al. "Novel Contact Force Sensor Incorporated in Irrigated Radiofrequency Ablation Catheter Predicts Lesion Size and Incidence of Steam Pop and Thrombus", Circulation: Arrhythmia and Electrophysiology, 1(5): 354-362, Published Online Dec. 2, 2008.

* cited by examiner

NORMAL

TEMPORARY DAMAGE

DESTROYED

METHOD AND SYSTEM FOR IMAGING A TISSUE USING ACOUSTO-ELECTRIC EFFECT

RELATED APPLICATIONS

This application claims the benefit of priority under 35 USC § 119(e) of U.S. Provisional Patent Application No. 62/576,775 filed on Oct. 25, 2017, the contents of which are incorporated by reference as if fully set forth herein in their entirety.

FIELD AND BACKGROUND OF THE INVENTION

The present invention, in some embodiments thereof, relates to means and methods for tissue analysis and characterization and, more particularly, but not exclusively, to means and methods for tissue analysis and characterization using acoustic energy and/or pressure waves.

Cardiac catheter ablation is a treatment for different kinds of cardiac arrhythmias, among which: supraventricular tachycardia (SVT), atrial flatter (AFL), atrial fibrillation (AF) and ventricular tachycardia (VT). Ablation procedures produce an injury in a heart tissue, by applying thermal or mechanical energy, using methods based on, for example, radiofrequency (RF ablation), laser or intense cooling (Cryoablation). While 90-95% success rate is achieved in catheter ablation procedures for SVT and typical AFL, where the target ablation region is localized, apparently for more complex arrhythmia mechanisms such as AF arrhythmia recurrence is in 50-70% of the cases. Apparently, two of the major causes of this low efficacy are apparent limitations in anatomical and electrical mapping of the heart and the inability to create a durable lesion and assess its dimensions, effectiveness, transmurality and continuity. It has been proposed that the goal is a complete destruction of the arrhythmogenic substrate, without producing collateral injury, such as a puncture of a heart chamber wall.

Several intra-procedural methods for assessing completeness of lesion formation have been proposed including: methods based on change in electrogram (EGM) amplitude or morphology or increase in pacing threshold at the site. Apparently, these methods are based on voltage measurements and hence suffer from sensitivity to changes in the cardiac activation sequence.

Real time MRI, and MRI thermography, are considered modalities for intra-procedural lesion assessment. Cardiac magnetic resonance (MR) imaging appears capable of delineating areas of permanent tissue damage caused by ablation; however, MRI entails the use of MRI safe catheters in specialized environment that makes it logistically complex.

Near-field ultrasonic imaging during RF ablation has been proposed as a modality for real-time visualization of evolving lesion, by using ultrasound transducers embedded on the catheter tip.

Many methods have been proposed for arrhythmia ablation lesion assessments, which are based on tissue impedance drop measurement. Apparently, both in RF and in cryogenic ablation procedures, the impedance decreases and electrical conductivity increases as the treated tissue becomes more necrotic, until reaching a point of tissue desiccation when impedance rises. Electrical impedance is a passive property of the myocardium and hence is not affected by cardiac activation sequence changes such as methods that are based on voltage measurements. Other methods have been proposed, which measure tissue electrical impedance "globally" between the ablating electrode and a cutaneous electrode patch. Impedance measured in this way, represents a weighted average of electrical resistivity of all tissues that constitute the electrical pathways between the two electrodes. Moreover, tissue characteristics influence impedance, for instance, the interstitial space has lower resistance than cell membranes, and hence the ratio between cellular and interstitial volumes influences tissue impedance. As a result, globally measured impedance drop had apparent limited success and was found by some to be a poor predictor of ablation lesion quality and size.

Several methods have been proposed for local measurement of myocardial impedance, using electrodes at the tip of a catheter. It has been shown that Local Bio-Impedance drop ($\Delta$LBI) correlates with the success of the ablation procedure: $\Delta$LBI is significantly larger for successful than unsuccessful lesions, where for instance in the left atrium: an average of 16$\Omega$ drop in Local Bio-Impedance was found typical of successful lesions, while a drop of 9$\Omega$ on the average, for unsuccessful lesions. Local Bio-Impedance was measured by injecting non-stimulatory alternating current (with amplitude of 5 microamperes and a frequency of 14.5 KHz) between two electrodes at the distal end and measurement of the resulting voltage between two other electrodes at the tip of the ablating catheter. The Local Bio-Impedance is the division of the measured voltage and the injected current.

U.S. Pat. No. 6,520,911 discloses a "system and method of imaging based on the interaction of ultrasonic pulses with a magnetic field. A static magnetic field is applied to an object having conductive properties. An ultrasound pulse is propagated into the object, and an electrical signal is detected which is related to the interaction of the ultrasound pulse local displacement of the conductive object and the magnetic field. Alternatively, and equivalently, an electrical pulse is propagated into the object, and an ultrasound signal is detected which is related to the interaction of the electrical pulse generated in the conductive object and the magnetic field. The acquired acoustic signals or the acquired electrical signals are processed to provide an image of the object. The acquired signals are dependent on local conductivity as well as local acoustic properties".

U.S. Pat. No. 6,645,144 discloses "methods for obtaining electroacoustic images of specimens. One method includes applying an acoustic wave to a specimen and forming an image based on an electroacoustically induced electric field or voltage. In another method, an electric field or voltage is applied to a specimen and an electroacoustically induced acoustic wave is measured to form an image. Apparatus suitable for obtaining electroacoustic images are disclosed as well as methods for distinguishing image contributions from the electroacoustic, thermoacoustic, and Hall effects".

U.S. Pat. No. 8,057,390 discloses "a current source density mapping system includes an ultrasound transducer emitting an ultrasound wave traveling along an ultrasound beam directed at a mapping field in a region of living tissue and an ultrasound pulser delivering a transmit pulse to said ultrasound transducer. The system includes a timing device producing controlled excitation of the transmit pulse; a plurality of recording electrodes positioned in contact with the living tissue detecting an acoustoelectric voltage signal generated at a bioelectric current source and within a focal zone of said ultrasound beam. An amplifier, operatively connected to the recording electrodes, amplifying the acoustoelectric voltage signal at a predetermined gain; and an analyzing component comprising a digitizer, a sampling device, a signal processor and a display unit operatively connected to the amplifier determining the location of the bioelectric current source by analyzing the acoustoelectric voltage signal detected by the recording electrodes in response to an interaction between the ultrasound wave and the presence of a current source in the mapping field".

U.S. Pat. No. 8,427,906 discloses "an ultrasound system that detects a characteristic of an ultrasound wave. The system includes a circuit member defining a sensing portion operable to be exposed to the ultrasound wave. The system also includes a current generating device that generates a current in the sensing portion of the circuit member. Furthermore, the system includes a voltage sensor that detects a voltage across the sensing portion due to the exposure to the ultrasound wave to thereby detect the characteristic of the ultrasound wave".

U.S. Patent Application No. 2002/0129655 discloses "a method and device for imaging based on the electroacoustic effect. The electroacoustic effect takes place when an ultrasonic wave passes through an electrolyte or colloidal suspension. The method and device of the invention produces images whereby a sound wave is generated at the surface of an object, and, as the wave progresses through the body a voltage is generated in time corresponding to the electroacoustic response of the body at a point in space and time corresponding to the position of the ultrasonic wave in the body. As pulses are launched into the body at different points in space, the signal sensed by an amplifier is used to generate an image".

U.S. Patent Application No. 2008/0183076 discloses "a current source density mapping system includes an ultrasound transducer emitting an ultrasound wave traveling along an ultrasound beam directed at a mapping field in a region of living tissue and an ultrasound pulser delivering a transmit pulse to said ultrasound transducer. The system includes a timing device producing controlled excitation of the transmit pulse; a plurality of recording electrodes positioned in contact with the living tissue detecting an acoustoelectric voltage signal generated at a bioelectric current source and within a focal zone of said ultrasound beam. An amplifier operatively connected to the recording electrodes amplifying the acoustoelectric voltage signal at a predetermined gain; and an analyzing component comprising a digitizer, a sampling device, a signal processor and a display unit operatively connected to the amplifier determining the location of the bioelectric current source by analyzing the acoustoelectric voltage signal detected by the recording electrodes in response to an interaction between the ultrasound wave and the presence of a current source in the mapping field".

Additional background art includes:

[1] Spector P, Reynolds M R, Calkins H, Sondhi M, Xu Y, Martin A, Williams C J, Sledge I. Meta-analysis of ablation of atrial flutter and supraventricular tachycardia. The American journal of cardiology 2009; 104: 671-677.

[2] Ganesan A N, Shipp N J, Brooks A G, Kuklik P, Lau D H, Lim H S, Sullivan T, Roberts-Thomson K C, Sanders P. Long-term outcomes of catheter ablation of atrial fibrillation: A systematic review and meta-analysis. Journal of the American Heart Association 2013; 2:e004549.

[3] Stevenson W G, Wilber D J, Natale A, Jackman W M, Marchlinski F E, Talbert T, Gonzalez M D, Worley S J, Daoud E G, Hwang C, Schuger C, Bump T E, Jazayeri M, Tomassoni G F, Kopelman H A, Soejima K, Nakagawa H. Irrigated radiofrequency catheter ablation guided by electroanatomic mapping for recurrent ventricular tachycardia after myocardial infarction: The multicenter thermocool ventricular tachycardia ablation trial. Circulation 2008; 118:2773-2782.

[4] Saurabh Kumar, MBBS, PhD, Chirag R. Barbhaiya, MD, Samuel Balindger, MD, Roy M. John M D, PhD, Laurence M. Epstein, MD, Bruce A. Koplan, MD, Usha B. Tedrow, MD, William G. Stevenson, MD, Gregory F. Michaud, MD. Better Lesion Creation And Assessment During Catheter Ablation. Journal of Atrial fibrillation October-November 2015, Volume 8, Issue 3.

[5] Sapp J L, Soejima K, Cooper J M, Epstein L M, Stevenson W G. Ablation lesion size correlates with pacing threshold: A physiological basis for use of pacing to assess ablation lesions. Pacing and clinical electrophysiology: PACE 2004; 27:933-937.

[6] Delacretaz E, Soejima K, Brunckhorst C B, Maisel W H, Friedman P L, Stevenson W G. Assessment of radiofrequency ablation effect from unipolar pacing threshold. Pacing and clinical electrophysiology: PACE 2003; 26:1993-1996.

[7] Ranjan R, Kato R, Zviman M M, Dickfeld T M, Roguin A, Berger R D, Tomaselli G F, Halperin H R. Gaps in the ablation line as a potential cause of recovery from electrical isolation and their visualization using mri. Circulation Arrhythmia and electrophysiology 2011; 4:279-286.

[8] Ranjan R, Kholmovski E G, Blauer J, Vijayakumar S, Volland N A, Salama M E, Parker D L, MacLeod R, Marrouche N F. Identification and acute targeting of gaps in atrial ablation lesion sets using a real-time magnetic resonance imaging system. Circulation Arrhythmia and electrophysiology 2012; 5:1130-1135.

[9] Kolandaivelu A, Zviman M M, Castro V, Lardo A C, Berger R D, Halperin H R. Noninvasive assessment of tissue heating during cardiac radiofrequency ablation using mri thermography. Circulation Arrhythmia and electrophysiology 2010; 3:521-529.

[10] Haines D E, Wright M, Harks E, et al. Near field ultrasound imaging during radiofrequency catheter ablation: Tissue thickness and epicardial wall visualization and assessment of radiofrequency ablation lesion formation and depth. Circ Arrhythm Electrophysiol. 2017; 10:e005295.

[11] Harvey M, Kim Y, Sousa J, et al. Impedance monitoring during radiofrequency catheter ablation in humans. Pacing Clin Electrophysiol. 1992; 15:22-27.

[12] Thiagalingam A, D'Avila A, Foley L, Guerrero J L, Lambert H, Leo G, Ruskin J N, Reddy V Y. Importance of catheter contact force during irrigated radiofrequency ablation: Evaluation in a porcine ex vivo model using a force-sensing catheter. Journal of cardiovascular electrophysiology 2010; 21:806-811.

[13] Yokoyama K, Nakagawa H, Shah D C, Lambert H, Leo G, Aeby N, Ikeda A, Pitha J V, Sharma T, Lazzara R, Jackman W M. Novel contact force sensor incorporated in irrigated radiofrequency ablation catheter predicts lesion size and incidence of steam pop and thrombus. Circulation Arrhythmia and electrophysiology 2008; 1:354-362.

[14] Dumas Iii J H, Himel Iv H D, Kiser A C, Quint S R, Knisley S B. Myocardial electrical impedance as a predictor of the quality of rf-induced linear lesions. Physiological measurement 2008; 29:1195-1207.

[15] Avitall B, Mughal K, Hare J, Helms R, Krum D. The effects of electrode-tissue contact on radiofrequency lesion generation. Pacing and clinical electrophysiology: PACE 1997; 20:2899-2910.

[16] Stagegaard N, Petersen H H, Chen X, Svendsen J H. Indication of the radiofrequency induced lesion size by pre-ablation measurements. Europace: European pacing, arrhythmias, and cardiac electrophysiology: journal of the working groups on cardiac pacing, arrhythmias, and cardiac cellular electrophysiology of the European Society of Cardiology 2005; 7:525-534.

[17] Atsushi Ikeda, MD, PhD; Hiroshi Nakagawa, MD, PhD; Hendrik Lambert, PhD; Dipen C. Shah, MD; Edouard Fonck, PhD; Aude Yulzari, MS; Tushar Sharma, MD, MPH; Jan V. Pitha, MD, PhD; Ralph Lazzara, MD; Warren M. Jackman, MD Relationship Between Catheter Contact Force and Radiofrequency Lesion Size and Incidence of Steam Pop in the Beating Canine Heart —Electrogram Amplitude, Impedance, and Electrode Temperature Are Poor Predictors of Electrode-Tissue Contact Force and Lesion Size. DOI: 10.1161/CIRCEP.113.001094.

[18] Warren M, Bragós R, Casas O, et al. Percutaneous electrocatheter technique for on-line detection of healed transmural myocardial infarction. Pacing Clin Electrophysiol PACE. 2000; 23:1283-1287.

[19] Wolf T, Gepstein L, Hayam G, et al. Three-dimensional endocardial impedance mapping: A new approach for myocardial infarction assessment. Am J Physiol Heart Circ Physiol. 2001; 280:H179-188.

[20] Martin C A, Martin R, Gajendragadkar P R, et al. First clinical use of novel ablation catheter incorporating local impedance data. J Cardiovasc Electrophysiol. 2018; 1-10. 2018; 2tp9s:1:/1/d9o7i.-o1rg2/ 0160..1h1tt1p1s/:j/c/de.o1i3.o6r5g/410.1111/ jce.13654.

SUMMARY OF THE INVENTION

According to an aspect of some embodiments of the invention, there is provided a system for tissue characterization using an acousto-electric effect comprising: at least one acoustic waveform generator; at least one waveform generation controller; at least one set of electrodes; at least one electric signal amplification circuitry connectable to at least one of said at least one set of electrodes to generate an amplified signal; and at least one signal processing unit for analyzing said amplified signal and to generate information indicative to at least one property of multiple locations within a target tissue taking into account said acousto-electric effect; wherein said at least one waveform includes a coded sequence of variations to be taken in consideration by said at least one signal processing unit.

According to some embodiments of the invention, said coded sequence of variations comprises a single narrow high peak auto-correlation at certain timing with low auto-correlation when not at said timing.

According to some embodiments of the invention, said coded sequence of variations comprises a single narrow high peak auto-correlation at certain timing with low auto-correlation when not at said timing.

According to some embodiments of the invention, different sequences are selected for different acoustic waveform generators.

According to some embodiments of the invention, there is a limitation to cross correlation between any two transducers at all delays.

According to some embodiments of the invention, said coded sequence of variations comprises a low maximal absolute value of cross correlation to all other sequences.

According to some embodiments of the invention, said low maximal absolute value of cross correlation provides the maximal signal to interference ratio.

According to some embodiments of the invention, at least one of said multiple location has no direct contact with any electrode.

According to some embodiments of the invention, said properties of said multiple locations are obtained within up to 10 milliseconds per location on average.

According to some embodiments of the invention, said information indicative to at least one property of multiple locations within a target tissue is presented as a two-dimensional map.

According to some embodiments of the invention, said two-dimensional map indicates an activation sequence of said tissue.

According to some embodiments of the invention, said information indicative to at least one property of multiple locations within a target tissue is presented as a three-dimensional map.

According to some embodiments of the invention, said three-dimensional map indicates an activation sequence of said tissue.

According to some embodiments of the invention, said three-dimensional map is superimposed and aligned in three dimensions with an anatomical map of the tissue.

According to some embodiments of the invention, said anatomical map of the tissue is generated by ultrasound.

According to some embodiments of the invention, said acoustic waveform generator is embedded in the ultrasonic system that provides the anatomical map.

According to some embodiments of the invention, said anatomical map of the tissue is generated by at least one of CT, ultrasound, MRI.

According to some embodiments of the invention, said at least one property is selected from the group consisting of: tissue viability state; effectiveness of ablation procedure; effective depth of an ablation; whether an ablation was trans-mural; ablation damage to surrounding non-target tissue; tissue electrical activity state; tissue electrical action potential; tissue electrical propagation velocity; tissue electrical propagation direction; tissue electrical conductance; tissue electrical impedance.

According to some embodiments of the invention, said properties of at least one of said multiple locations comprise one or more of the conditions selected from group consisting of normal, alive, dead, scar, fibrotic, edema, alive and functioning, alive and not functioning.

According to some embodiments of the invention, said properties of at least one of said multiple locations comprise at least one of the conditions selected from a list comprising rest, triggered, contracting, relaxing, in refractory period, in relative refractory period.

According to some embodiments of the invention, said properties of at least two of said multiple locations indicate a relative timing of tissue activity.

According to some embodiments of the invention, said properties of at least two of said multiple locations indicate a map with at least two directions with relative timing (earlier/later) of tissue activity.

According to some embodiments of the invention, said properties of at least two of said multiple locations indicate a quality of an isolation line generated by tissue ablation.

According to some embodiments of the invention, said properties of said multiple locations are obtained from about 0.5 seconds to about 100 seconds per location on average.

According to some embodiments of the invention, said at least one acoustic waveform generator generates pulses or waveforms with repetition rate from about 100 Hz to about 10 MHz.

According to some embodiments of the invention, said at least one acoustic waveform generator generates patterns that repeat every up to from about 100 microseconds to about 10 milliseconds.

According to some embodiments of the invention, said at least one acoustic waveform generator generates pulses or waveforms with an envelope having the majority of the energy within a duration of from about 1 microsecond to about 10 microseconds.

According to some embodiments of the invention, said at least one acoustic waveform generator generates one or more waveforms having an envelope having the majority of the energy over a time period longer than from about 20 microseconds to about 1 second with auto-correlation having a peak with a duration shorter than 10 microseconds.

According to some embodiments of the invention, said envelope is practically a continuous wave.

According to some embodiments of the invention, said auto-correlation peak duration is shorter than 5 microseconds.

According to some embodiments of the invention, said one or more waveforms includes on-off keying of pulses.

According to some embodiments of the invention, said one or more waveforms includes a barker sequence.

According to some embodiments of the invention, said one or more waveforms includes a chirp.

According to some embodiments of the invention, said one or more waveforms includes a random pattern.

According to some embodiments of the invention, at least one of said at least one signal processing unit include instructions to correlate between the amplified electric signal and the ultrasonic waveform.

According to some embodiments of the invention, the correlation provides time resolution of the analyzed acousto-electric effect of 10 microseconds or lower.

According to some embodiments of the invention, at least one of said at least one signal processing unit calculates information about said properties at a certain distance along the acoustic wave propagation path based on the timing of the analyzed acousto-electric signal.

According to some embodiments of the invention, said duration defines the depth resolution of the properties calculated per location in the tissue along the acoustic wave propagation path.

According to some embodiments of the invention, said time resolution defines the depth resolution of the properties calculated per location in the tissue along the acoustic wave propagation path.

According to some embodiments of the invention, said system provides information about said properties at a depth resolution of from about 0.5 millimeters to about 20 millimeters along the acoustic wave propagation path by controlling the time of reading of the acoustic wave.

According to some embodiments of the invention, said acoustic waveform is delivered in a focused manner at an energy level sufficient to trigger tissue activation at a target location.

According to some embodiments of the invention, the outputs of said signal amplification circuitry is integrated over multiple instances of the cycle of operation of said system, to amplify and/or attenuate certain information components.

According to some embodiments of the invention, waveform generator outputs a pre-determined pattern.

According to some embodiments of the invention, said pattern consists of a 'chirp' signal, wherein the signal frequency increases over time.

According to some embodiments of the invention, the output generation of acoustic waves is continuous and the signal processing and/or analysis matches the received electric signal with generated output at various time delays to recover the acousto-electric information corresponding to different locations.

According to some embodiments of the invention, at least one of the signal generated by said waveform generator and the analysis of the signal output of said signal amplification circuitry include utilization of at least one method selected from modulation and demodulation, FSK, continuous phase, varying phase, FM.

According to some embodiments of the invention, said tissue is a cardiac tissue.

According to an aspect of some embodiments of the invention, there is provided a method of tissue characterization using an acousto-electric effect comprising: irradiating said tissue with an acoustic waveform; detecting an acoustoelectric voltage signal by means of at least one set of electrodes; processing and analyzing said acoustoelectric voltage signal; generating information indicative to at least one property of multiple locations within said tissue taking into account said acousto-electric effect; wherein said method comprises providing said acoustic waveform including a coded sequence of variations.

According to some embodiments of the invention, said coded sequence of variations comprises a single narrow high peak auto-correlation at certain timing with low auto-correlation when not at said timing.

According to some embodiments of the invention, said coded sequence of variations comprises a single narrow high peak auto-correlation at certain timing with low auto-correlation when not at said timing.

According to some embodiments of the invention, different sequences are selected for different acoustic waveform generators.

According to some embodiments of the invention, there is a limitation to cross correlation between any two transducers at all delays.

According to some embodiments of the invention, said coded sequence of variations comprises a low maximal absolute value of cross correlation to all other sequences.

According to some embodiments of the invention, said low maximal absolute value of cross correlation provides the maximal signal to interference ratio.

According to some embodiments of the invention, said generating information indicative to at least one property comprises generating information indicative to tissue viability state.

According to some embodiments of the invention, said generating information indicative to at least one property comprises assessing whether an ablation of said tissue was effective.

According to some embodiments of the invention, said generating information indicative to at least one property comprises assessing effective depth of an ablation.

According to some embodiments of the invention, said generating information indicative to at least one property comprises assessing whether an ablation was trans-mural.

According to some embodiments of the invention, said generating information indicative to at least one property comprises assessing ablation damage to surrounding non-target tissue.

According to some embodiments of the invention, said generating information indicative to at least one property comprises assessing whether tissue is in one or more of the conditions selected from a list including normal, alive, dead, scar, fibrotic, edema, alive and functioning, alive and not functioning.

According to some embodiments of the invention, said generating information indicative to at least one property comprises determining if the tissue is in at least one of the conditions selected from a list comprising rest, triggered, contracting, relaxing, in refractory period, in relative refractory period.

According to some embodiments of the invention, said generating information indicative to at least one property comprises assessing tissue electrical impedance.

According to some embodiments of the invention, properties of at least two of said multiple locations indicate a direction of electrical propagation within the tissue.

According to some embodiments of the invention, properties of at least two of said multiple locations indicate a time relation of activation between said at least two of said multiple locations.

According to some embodiments of the invention, properties of at least two of said multiple locations are presented as a two-dimensional map.

According to some embodiments of the invention, said two-dimensional map indicates an activation sequence of said tissue.

According to some embodiments of the invention, said generating information comprises generating said multiple locations as a three-dimensional map.

According to some embodiments of the invention, said three-dimensional map indicates an activation sequence of said tissue.

According to some embodiments of the invention, further comprising superimposing and aligning in three dimensions said three-dimensional map with an anatomical map of the tissue.

According to some embodiments of the invention, said anatomical map of the tissue is generated by ultrasound.

According to some embodiments of the invention, said anatomical map of the tissue is generated by at least one of CT, ultrasound, MRI.

According to some embodiments of the invention, said generating information indicative to at least one property comprises determining if the tissue is in at least one of the conditions selected from a list comprising rest, triggered, contracting, relaxing, in refractory period, in relative refractory period.

According to some embodiments of the invention, said generating information indicative to at least one property further comprises evaluating said information relative to at least one reference selected from the group consisting of: timing of a self-activated tissue; timing of a pacing signal; timing of a said trigger of said tissue activation.

According to some embodiments of the invention, the method further comprises using at least one of said at least one set of electrodes to deliver an electric field to said tissue and/or electric current through said tissue and at least one electric signal amplification circuitry generates amplified signal from the signals received through said at least one set of electrodes; said amplified signal is being analyzed in a manner that is responsive to the delivered field and/or current, and is indicative of tissue property at said tissue.

According to an aspect of some embodiments of the invention, there is provided a method of performing an ablation procedure comprising: using an ablation tool; and using acousto-electric effect for determining tissue viability state.

According to some embodiments of the invention, using acousto-electric effect further comprises using acousto-electric effect to guide said ablation procedure.

According to some embodiments of the invention, said determining is at a distance from said ablation tool.

According to some embodiments of the invention, said determining is performed at multiple locations at a depth of at least 1 mm inside the tissue.

According to some embodiments of the invention, said determining is performed at multiple locations along a path of at least 1 mm and up to 20 mm away from the ablation tool.

According to some embodiments of the invention, said determining is performed at multiple locations at distance of more than 1 centimeter from said ablation tool.

According to some embodiments of the invention, providing at least one source of an acoustic waveform.

According to some embodiments of the invention, said at least one source of an acoustic waveform is part of the ablation tool.

According to some embodiments of the invention, said at least one source of an acoustic waveform is intrabody and is located on a separate tool than said ablation tool.

According to some embodiments of the invention, said at least one source of an acoustic waveform is extracorporeal.

According to some embodiments of the invention, further comprising providing one or more set of electrodes for receiving electrical signal and or delivering an electric current.

According to some embodiments of the invention, at least one of said electrodes is part of the ablation tool.

According to some embodiments of the invention, at least one of said electrodes is intrabody on a separate tool than the ablation tool.

According to some embodiments of the invention, at least one of said electrodes is extracorporeal.

According to some embodiments of the invention, comprising providing an acoustic waveform including a coded sequence of variations.

According to some embodiments of the invention, the method further comprises providing a display showing said multiple locations as a three-dimensional map.

According to some embodiments of the invention, the method further comprising superimposing and aligning in three dimensions said three-dimensional map with an anatomical map of the tissue.

According to an aspect of some embodiments of the invention, there is provided a system for tissue characterization using an acousto-electric effect including at least one ultrasonic waveform generator, at least one waveform generation controller, at least one set of electrodes, at least one electric signal amplification circuitry connectable to at least one of the at least one set of electrodes to generate an amplified signal, and at least one signal processing unit for analyzing the amplified signal and to generate information related to properties of multiple locations within a target tissue, wherein at least one of the multiple location has no direct contact with any electrode, and wherein the properties of the multiple locations are obtained within up to 10 seconds per location on average.

According to some embodiments of the invention, the properties of at least one of the multiple locations comprise tissue viability state.

According to some embodiments of the invention, the properties of at least one of the multiple locations comprise assessment of whether an ablation of the tissue was effective.

According to some embodiments of the invention, the properties of at least one of the multiple locations comprise assessment of effective depth of an ablation.

According to some embodiments of the invention, the properties of at least one of the multiple locations comprise assessment of whether an ablation was trans-mural.

According to some embodiments of the invention, the properties of at least one of the multiple locations comprise assessment of ablation damage to surrounding non-target tissue.

According to some embodiments of the invention, the properties of at least one of the multiple locations comprise assessment of whether tissue is in one or more of the conditions selected from a list including normal, alive, dead, scar, fibrotic, edema, alive and functioning, alive and not functioning.

According to some embodiments of the invention, the properties of at least one of the multiple locations comprise tissue electrical activity state.

According to some embodiments of the invention, the properties of at least one of the multiple locations comprise tissue viability state.

According to some embodiments of the invention, the properties of at least one of the multiple locations comprise tissue electrical action potential.

According to some embodiments of the invention, the properties of at least one of the multiple locations comprise determining is the tissue is in at least one of the conditions selected from a list including rest, triggered, contracting, relaxing, in refractory period, in relative refractory period.

According to some embodiments of the invention, the properties of at least one of the multiple locations comprise tissue electrical propagation velocity.

According to some embodiments of the invention, the properties of at least one of the multiple locations comprise tissue electrical propagation direction.

According to some embodiments of the invention, the properties of at least one of the multiple locations comprise tissue electrical conductance.

According to some embodiments of the invention, the properties of at least one of the multiple locations comprise tissue electrical impedance.

According to some embodiments of the invention, the properties of at least two of the multiple locations indicate a direction of electrical propagation within the tissue.

According to some embodiments of the invention, the properties of at least two of the multiple locations indicate a time relation of activation between the at least two of the multiple locations.

According to some embodiments of the invention, the properties of at least two of the multiple locations are presented as a two dimensional map indicating the activation sequence of the tissue.

According to some embodiments of the invention, the properties of at least two of the multiple locations are presented as a three dimensional map indicating the activation sequence of the tissue.

According to some embodiments of the invention, the three dimensional map is superimposed and aligned in three dimensions with an anatomical map of the tissue.

According to some embodiments of the invention, the anatomical map of the tissue is generated by ultrasound.

According to some embodiments of the invention, the ultrasonic waveform generator is embedded in the ultrasonic system that provides the anatomical map.

According to some embodiments of the invention, the anatomical map of the tissue is generated by at least one of CT, ultrasound, MRI.

According to some embodiments of the invention, the three dimensional map is superimposed with an anatomical map of the tissue.

According to some embodiments of the invention, the properties of at least two of the multiple locations indicate a recommended direction for moving a catheter.

According to some embodiments of the invention, the properties of at least two of the multiple locations indicate a relative timing of tissue activity.

According to some embodiments of the invention, the properties of at least two of the multiple locations indicate a map with at least two directions with relative timing (earlier/later) of tissue activity.

According to some embodiments of the invention, the two directions comprise at least right and left relative to a catheter location and orientation.

According to some embodiments of the invention, the two directions comprise at least up and down relative to a catheter location and orientation.

According to some embodiments of the invention, the properties of at least two of the multiple locations indicate a quality of an isolation line generated by tissue ablation.

According to some embodiments of the invention, the properties of the multiple locations are obtained within up to 1 second per location on average.

According to some embodiments of the invention, the properties of the multiple locations are obtained within up to 100 milliseconds per location on average.

According to some embodiments of the invention, the properties of the multiple locations are obtained within up to 10 milliseconds per location on average.

According to some embodiments of the invention, the properties of the multiple locations are obtained within up to 1 millisecond per location on average.

According to some embodiments of the invention, the at least one ultrasonic waveform generator generates pulses or waveforms with repetition rate of 100 Hz or higher.

According to some embodiments of the invention, the repetition is at a rate of 300 Hz or higher.

According to some embodiments of the invention, the repetition is at a rate of 1 KHz or higher.

According to some embodiments of the invention, the repetition is at a rate of 5 KHz or higher.

According to some embodiments of the invention, the repetition is at a rate of 10 KHz or higher.

According to some embodiments of the invention, the at least one ultrasonic waveform generator generates patterns that substantially repeat every up to 10 milliseconds.

According to some embodiments of the invention, the repetition is every up to 3 milliseconds.

According to some embodiments of the invention, the repetition is every up to 1 milliseconds.

According to some embodiments of the invention, the repetition is up to 200 microseconds.

According to some embodiments of the invention, the repetition is up to 100 microseconds.

According to some embodiments of the invention, the at least one ultrasonic waveform generator generates pulses or waveforms with an envelope having the majority of the energy within a duration of up to 10 microseconds.

According to some embodiments of the invention, the envelope having the majority of the energy within a duration of up to 5 microseconds.

According to some embodiments of the invention, the envelope having the majority of the energy within a duration of up to 3 microseconds.

According to some embodiments of the invention, the envelope having the majority of the energy within a duration of up to 1 microseconds.

According to some embodiments of the invention, the at least one ultrasonic waveform generator generates one or more waveforms having an envelope having the majority of the energy over a time period longer than 20 microseconds with auto-correlation having a peak with a duration shorter than 1 microsecond.

According to some embodiments of the invention, the envelope having the majority of the energy over a time period longer than 1 second.

According to some embodiments of the invention, the one or more waveforms includes variation of phase.

According to some embodiments of the invention, the one or more waveforms includes a coded sequence having a single narrow high peak auto-correlation at certain timing with low auto-correlation when not at the timing.

According to some embodiments of the invention, the envelope having the majority of the energy over a time period longer than 50 microseconds.

According to some embodiments of the invention, the envelope having the majority of the energy over a time period longer than 100 microseconds.

According to some embodiments of the invention, the envelope having the majority of the energy over a time period longer than 500 microseconds.

According to some embodiments of the invention, the envelope having the majority of the energy over a time period longer than 5 millisecond.

According to some embodiments of the invention, the envelope having the majority of the energy over a time period longer than 10 millisecond.

According to some embodiments of the invention, the envelope having the majority of the energy over a time period longer than 50 millisecond.

According to some embodiments of the invention, the envelope having the majority of the energy over a time period longer than 1 second.

According to some embodiments of the invention, the envelope is practically a continuous wave.

According to some embodiments of the invention, the auto-correlation peak duration is shorter than 5 microseconds.

According to some embodiments of the invention, the auto-correlation peak duration is shorter than 3 microseconds.

According to some embodiments of the invention, the auto-correlation peak duration is shorter than 1 microsecond.

According to some embodiments of the invention, the one or more waveforms includes on-off keying of pulses.

According to some embodiments of the invention, the one or more waveforms includes variation of frequencies.

According to some embodiments of the invention, the one or more waveforms includes variation of amplitudes.

According to some embodiments of the invention, the one or more waveforms includes a coded sequence of variations having a single narrow high peak auto-correlation at certain timing with low auto-correlation when not at the timing.

According to some embodiments of the invention, the one or more waveforms includes a barker sequence.

According to some embodiments of the invention, the one or more waveforms includes a barker sequence.

According to some embodiments of the invention, the one or more waveforms includes chirp.

According to some embodiments of the invention, the one or more waveforms includes a random pattern.

According to some embodiments of the invention, at least one of the at least one signal processing unit include correlation between the amplified electric signal and the ultrasonic waveform.

According to some embodiments of the invention, the correlation provides time resolution of the analyzed acousto-electric effect of 10 microseconds or better.

According to some embodiments of the invention, the correlation provides time resolution of the analyzed acousto-electric effect of 5 microseconds or better.

According to some embodiments of the invention, the correlation provides time resolution of the analyzed acousto-electric effect of 3 microseconds or better.

According to some embodiments of the invention, the correlation provides time resolution of the analyzed acousto-electric effect of 2 microseconds or better.

According to some embodiments of the invention, the correlation provides time resolution of the analyzed acousto-electric effect of 1 microseconds or better.

According to some embodiments of the invention, the correlation provides time resolution of the analyzed acousto-electric effect of 0.5 microseconds or better.

According to some embodiments of the invention, at least one of the at least one signal processing unit calculates information about the properties at a certain distance along the acoustic wave propagation path based on the timing of the analyzed acousto-electric signal.

According to some embodiments of the invention, the duration defines the depth resolution of the properties calculated per location in the tissue along the acoustic wave propagation path.

According to some embodiments of the invention, the time resolution defines the depth resolution of the properties calculated per location in the tissue along the acoustic wave propagation path.

According to some embodiments of the invention, the system provides information about the properties at a depth resolution of 20 millimeters or better along the acoustic wave propagation path.

According to some embodiments of the invention, the depth resolution is 10 millimeters or better.

According to some embodiments of the invention, the depth resolution is 5 millimeters or better.

According to some embodiments of the invention, the depth resolution is 3 millimeters or better.

According to some embodiments of the invention, the depth resolution is 2 millimeters or better.

According to some embodiments of the invention, the depth resolution is 1 millimeters or better.

According to some embodiments of the invention, the depth resolution is 0.5 millimeters or better.

According to some embodiments of the invention, the ultrasonic waveform is delivered in a focused manner at an energy level sufficient to trigger tissue activation at a target location.

According to some embodiments of the invention, the triggering paces the target tissue.

According to some embodiments of the invention, the triggering is applied to multiple locations to pace the target tissue in multiple sites.

According to some embodiments of the invention, the pacing of multiple sites synchronizes sites.

According to some embodiments of the invention, the triggering is provided multiple times to generated programmed stimulation.

According to some embodiments of the invention, the properties are evaluated relative to a reference timing of a self-activated tissue.

According to some embodiments of the invention, the properties are evaluated relative to a reference timing of a pacing signal.

According to some embodiments of the invention, the properties are evaluated relative to a reference timing of the trigger of the tissue activation.

According to some embodiments of the invention, the at least one electric signal amplification circuitry connectable to at least one of the at least one set of electrodes.

According to some embodiments of the invention, the signal amplification circuitry is gated to be blanked during the generation of the waveform generator output signal, and be active during specified time period after the generation of the waveform generator output signal.

According to some embodiments of the invention, the specific time period starts at a specified delay from the generation of waveform generator output signal.

According to some embodiments of the invention, the specific time period is up to the maximum anticipated time for acoustic waves to propagate acoustically to the tissue of interest.

According to some embodiments of the invention, the outputs of the signal amplification circuitry is integrated over multiple instances of the cycle of operation of the system, to amplify and/or attenuate certain information components.

According to some embodiments of the invention, the waveform generator outputs a pre-determined pattern According to some embodiments of the invention, the pattern consists of a 'chirp' signal, wherein the signal frequency increases over time.

According to some embodiments of the invention, the output generation signal is used as a reference signal in the analysis of the signal picked up by the electrodes.

According to some embodiments of the invention, the output generation signal is used as a reference signal in the amplification process of the signal picked up by the electrodes.

According to some embodiments of the invention, the output generation of acoustic waves is continuous and the signal processing and/or analysis matches the received electric signal with generated output at various time delays to recover the acousto-electric information corresponding to different locations.

According to some embodiments of the invention, at least one of the signal generated by the waveform generator and the analysis of the signal output of the signal amplification circuitry include equalization and compensation for the acoustic wave propagation decay and distortions over the propagation distance.

According to some embodiments of the invention, at least one of the signal generated by the waveform generator and the analysis of the signal output of the signal amplification circuitry include utilization of at least one method selected from modulation and demodulation, FSK, continuous phase, varying phase, FM.

According to some embodiments of the invention, at least one of the at least one set of electrodes is used to deliver an electric field to the tissue and/or electric current through the tissue and at least one of the at least one electric signal amplification circuitry generates amplified signal from the signals received through at least one set of electrodes, the amplified signal is being analyzed in a manner that is responsive to the delivered field and/or current, and is indicative of tissue property at the target location.

According to some embodiments of the invention, the properties of at least one of the multiple locations comprise tissue temperature.

According to some embodiments of the invention, the properties of at least one of the multiple locations comprise tissue temperature changes over time.

According to some embodiments of the invention, the properties of at least one of the multiple locations comprise tissue fluid concentration.

According to some embodiments of the invention, the properties of at least one of the multiple locations comprise tissue changes over time in fluid concentration.

According to some embodiments of the invention, the properties of at least one of the multiple locations comprise tissue ion concentration.

According to some embodiments of the invention, the properties of at least one of the multiple locations comprise tissue changes over time in ion concentration.

According to some embodiments of the invention, the properties of at least one of the multiple locations comprise tissue electrolyte concentration.

According to some embodiments of the invention, the properties of at least one of the multiple locations comprise tissue changes over time in electrolyte concentration.

According to some embodiments of the invention, the system includes motion compensation mechanism.

According to some embodiments of the invention, the motion compensation mechanism compensates for local catheter motion.

According to some embodiments of the invention, the motion compensation mechanism compensates for muscle motion.

According to some embodiments of the invention, the motion compensation mechanism compensates for heart chamber motion.

According to some embodiments of the invention, the motion compensation mechanism compensates for blood motion.

According to some embodiments of the invention, the motion compensation mechanism compensates for respiratory motion.

According to some embodiments of the invention, the motion compensation mechanism compensates for cyclic cardiac motion.

According to some embodiments of the invention, the motion compensation mechanism utilizes information about motion based on local ultrasound measurement and/or imaging.

According to some embodiments of the invention, the motion compensation mechanism utilizes information about motion based on wider-angle ultrasound imaging of one or more heart chambers.

According to some embodiments of the invention, the motion compensation mechanism utilizes information about motion based on local ultrasound measurement.

According to some embodiments of the invention, the motion compensation mechanism utilizes information about motion based on a reference source.

According to some embodiments of the invention, the motion compensation is performed as part of the analysis.

According to some embodiments of the invention, the motion compensation is performed as part of the signal integration.

According to some embodiments of the invention, the motion compensation is performed as part of the preprocessing prior to analysis.

According to some embodiments of the invention, the motion compensation is performed as part of the display.

According to some embodiments of the invention, the ultrasonic waveform generator includes one or more ultrasonic transducers.

According to some embodiments of the invention, at least one of the one or more ultrasonic transducers comprise one or more piezo-electric elements.

According to some embodiments of the invention, at least one of the one or more ultrasonic transducers comprise one or more capacitive micro-machine ultrasonic transducers.

According to some embodiments of the invention, at least one of the one or more ultrasonic transducers comprise one or more piezo-electric micro-machine ultrasonic transducers.

According to some embodiments of the invention, at least one of the one or more ultrasonic transducers is positioned extra-corporeal.

According to some embodiments of the invention, at least one of the one or more ultrasonic transducers is positioned intra-luminally.

According to some embodiments of the invention, at least one of the one or more ultrasonic transducers is positioned trans-esophageal.

According to some embodiments of the invention, at least one of the one or more ultrasonic transducers is positioned intra-body.

According to some embodiments of the invention, at least one of the one or more ultrasonic transducers is as part of a catheter.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product.

Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such acquiring an image employing an intraoral scanner, might be expected to use completely different methods, e.g., making use of expert knowledge and/or the pattern recognition capabilities of the human brain, which would be vastly more efficient than manually going through the steps of the methods described herein.

DESCRIPTION OF SPECIFIC EMBODIMENTS OF THE INVENTION

Figure 1:
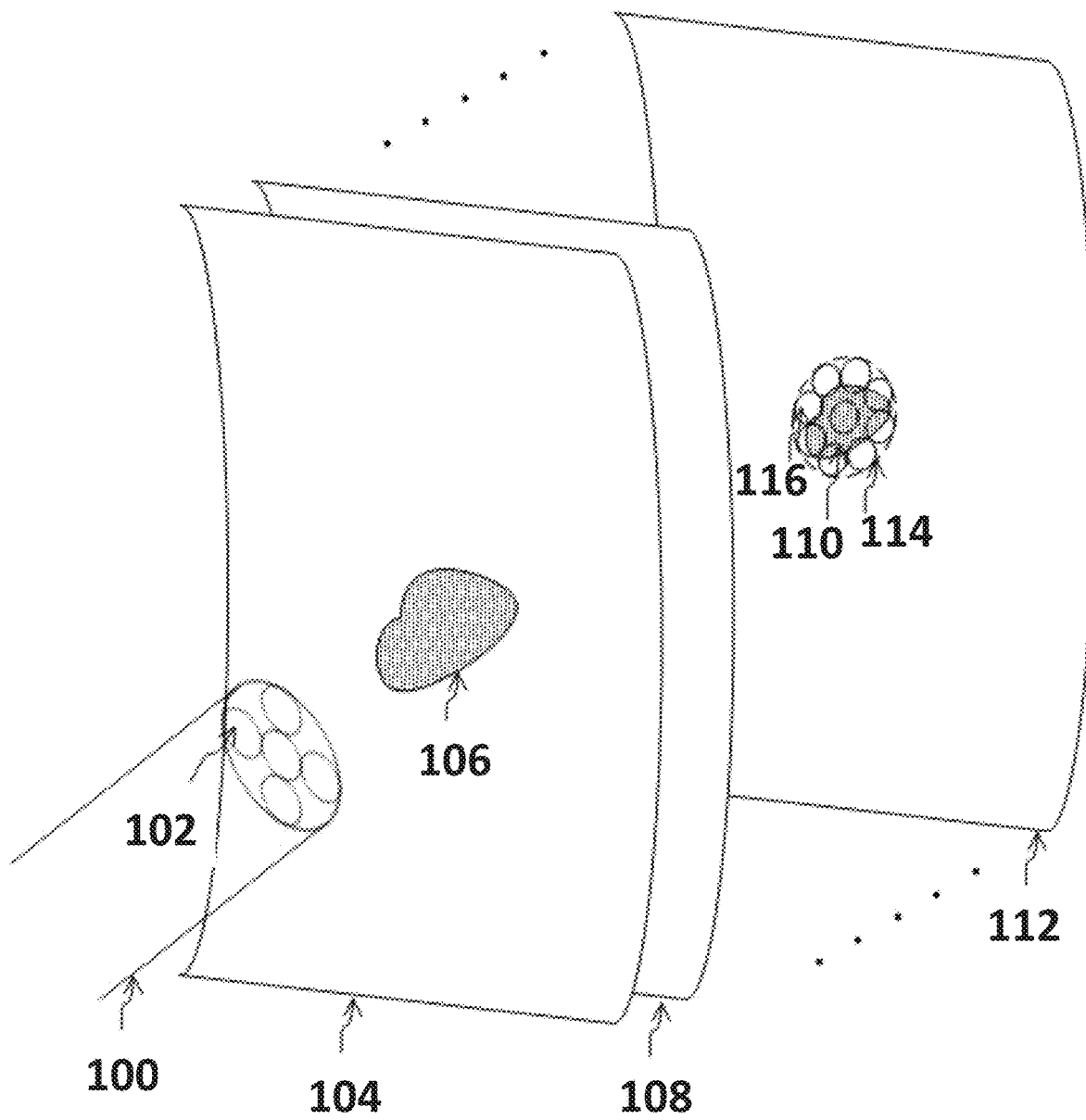
FIG. 1 is a schematic representation of the use of focused ultrasound for the localization of electrical property estimation of the tissue, according to some embodiments of the present invention.

The present invention, in some embodiments thereof, relates to means and methods for tissue analysis and characterization and, more particularly, but not exclusively, to means and methods for tissue analysis and characterization using acoustic energy and/or pressure waves.

Overview

An aspect of some embodiments of the present invention relates to tissue characterization using acoustic waves. In some embodiments, a 2D and/or 3D visualization of the tissue characteristics is generated following the use of acoustic waves. In some embodiments, coding schemes for the acoustic wave and decoding methods for the LBI estimation are used. In some embodiments, acoustic waves are directed at a target tissue and/or organ, and the tissue characterization is derived based on the impact of the acoustic waves on the target. In some embodiments, the acoustic waves produce electric waves in the target, while an array of electrodes are placed to sense the electric wave. In some embodiments, tissue characterization is achieved by analyzing the electric wave. In some embodiments, analysis of the electrical wave is performed with and/or without directly contacting the tissue. Additionally or alternatively, an electrical current may be generated and/or inducted, through transmitting electrodes, to achieve tissue characterization by means of impedance measure. In some embodiments, characterization of the tissue includes evaluating properties of the tissue, for example, tissue dielectric properties, tissue electrical activity, tissue action potential properties, tissue action potential propagation properties, tissue activation profile, tissue activity timing and relative timing of multiple locations within the tissue, tissue impedance and/or conductivity, tissue viability and/or tissue response to ablation and/or tissue response to stimulation and/or response to a treatment.

An aspect of some embodiments of the present invention relates to tissue characterization using acoustic waves. In some embodiments, coding schemes for the acoustic wave and decoding methods for the LBI estimation are used. In some embodiments, the tissue characterization is performed by analyzing at least one property of the tissue reflected by the behavior of the electric wave due to the acoustic wave. The electric wave is optionally, sensed by an array of electrodes. For example, properties being evaluated include, but not limited to, tissue dielectric properties, tissue electrical activity, tissue action potential properties, tissue action potential propagation properties, tissue activation profile, tissue activity timing and relative timing of multiple locations within the tissue, tissue impedance and/or conductivity, tissue viability and/or tissue response to ablation and/or tissue response to stimulation and/or response to a treatment. In some embodiments, the properties may be evaluated with and/or without directly contacting the tissue. In some embodiments, tissue properties are derived based on the modulation of the electrical properties driven by the acoustic wave at a given location and time. In some embodiments, properties may be evaluated in multiple locations serially and/or simultaneously. In some embodiments, the locality of measured properties is discerned according to the relationship between time dependent direction of the acoustic wave and the time dependent response of the tissue. For example, properties at different locations may be obtained to generate an image. Alternatively or additionally, properties at different locations may be for guidance for manipulating and/or positioning of a catheter and/or a treatment, and/or to generate diagnosis.

An aspect of some embodiments of the present invention relates to tissue characterization by modulating the electrical properties in a tissue, by exposing the tissue to an acoustic wave, at a given location and time. In some embodiments, the acoustic wave modulates electrical properties, for example one or more of distribution of charge carriers or mobility of charge carriers. In some embodiments, the acoustic wave drives the charge carriers into motion, resulting in transmission of electromagnetic waves, which properties are derived from those electrical properties. In some embodiments, applying electrical current serves to generate a strong signal that acts as a reference, with the variations in it resulting from the acoustic wave being the actual information-carrying signal. In some embodiments, characterization of the tissue includes evaluating properties of the tissue. In some embodiments, evaluation of properties of the tissue is performed in multiple locations serially and/or simultaneously. In some embodiments, the relationship between time dependent direction of the acoustic wave and the time dependent response of the tissue provides the evaluated relative location in the tissue. In some embodiments, the acoustic waves produce an electric signal in the target, while an array of electrodes are placed to sense the electric signal. In some embodiments, tissue characterization is achieved by analyzing the electric wave. In some embodiments, analysis of the electrical wave is performed with and/or without directly contacting the tissue. Additionally or alternatively, an electrical current may be generated and/or inducted, through transmitting electrodes, to achieve tissue characterization by means of impedance measure. In some embodiments, characterization of the tissue includes evaluating properties of the tissue, for example, tissue dielectric properties, tissue electrical activity, tissue action potential properties, tissue action potential propagation properties, tissue activation profile, tissue activity timing and relative timing of multiple locations within the tissue, tissue impedance and/or conductivity, tissue viability and/or tissue response to ablation and/or tissue response to stimulation and/or response to a treatment. In some embodiments, a 2D and/or 3D visualization of the tissue characteristics is generated following the use of acoustic waves. In some embodiments, coding schemes for the acoustic signal and decoding methods for the LBI estimation are used.

An aspect of some embodiments of the present invention relates to estimation of impedance at different specific depths and locations, in and around a specific target area and/or a specific lesion site. In some embodiments, estimation of impedance may provide a better indication of the status of the target area, the lesion development and the lesion site. In some embodiments, during ablation procedures, the measured values of impedance drop due to the death of the target tissue. In some embodiments, impedance drops are used for better assessment of the lesion with higher resolution and in 3-dimensions. In some embodiments, mapping the lesion depth is used to guide the decisions made by the physician during the procedure. In some embodiments, the thickness of the wall, where the impedance change is measured, is the indicator for reducing the risk of perforation.

Without limiting to a particular theoretical framework, an acousto-electric effect may be generated as a result of micro-vibrations and/or micro pressure waves traveling through the tissue and/or affecting local motion of the tissue. For example, effects may be generated by vibrations and/or changes to conductivity and/or changes of the mobility of a membrane to ions. Mechanisms of the effect may include, For example, compressing the local volume thus changing the ion density and/or changing the conductivity, and/or moving ions, and/or moving dipoles of ions. The various mechanisms may produce an electric field emitter.

In some embodiments, the measurements related to acousto-electric effect may include: measurements of a signal resulting from changes in the conductivity of the medium due to the presence of a pressure wave (sometimes called in the literature AEI—Acousto-Electric Interaction signal). For example, AEI may include evaluating changes to a measured voltage as a result of electric currents that flow through the tissue (for example the currents may be induced by electrodes and/or a signal generator, and/or by bio-electric currents). Alternatively or additionally, the measurements may include measuring a signal resulting from changes in charge density distribution (ions and dipoles concentrations)—within the cells and/or across membranes. For example, the changes in charge density distribution may result from vibration and motion of ions experiencing the forces produced by the (possibly periodic) displacement of the surrounding liquid (sometimes called in the literature UVP—Ultrasonic Vibration Potentials). In some embodiments, AEI may differ from UVP in the measured properties. In some conditions, it may be advantageous to use UVP and/or AEI. Some embodiments may employ AEI, some embodiments may employ UVP and some embodiments may employ both methodologies. For example, in real-time cardiac impedance/conductance mapping, AEI may be used with high level of induced currents. Optionally these induced currents will be consistent with the cardiac rhythm, for example, the induced currents may be configured to avoid causing abnormal and/or undesired pacing and/or arrhythmia.

For example, currents may be applied in a way that actually paces the heart, and/or currents may be applied during the absolute or relative refractory (QRS) period to avoid additional pacing. Alternatively or additionally an AEI based measurement may be based on the natural bio-currents. For example, bio-current based measured may be performed during the systole (e.g. using the R-wave of the ECG). In some cases, the electrical activity of the heart is relatively elevated during the systole. In some cases, natural bio-currents are quite weak (compared with induced currents). Techniques may be used to obtain real-time voltage readings of natural bio-currents AEI in the presence of the very noisy QRS period.

In some embodiments of the present invention, it is suggested, for example, to use AEI with either high frequency current, for example above 5 KHz and/or about 10 KHz and/or above 20 KHz. Hi frequency may avoid cardiac stimulation, at any time in the heart cycle. For example, high frequency AWI may be used during the systole and/or during the diastole and/or the resting phase of the heart. Alternatively or additionally, UVP may be used anytime in a heart cycle and/or specifically during the systole and/or specifically during the diastole and/or during the resting phase of the heart.

In some embodiments, signal generation, processing and/or coding approaches are provided to improve signal to noise ratio. In some embodiments, coding is used to measure multiple volumes of interest simultaneously. Optionally, measurement of multiple volumes of interest is performed without or with reduced degradation of the signal due to interference from one volume to another. Alternatively or additionally, time-domain signal analysis may be employed. For example, time domain analysis may facilitate real-time mapping of electrical activity of the tissue.

In some embodiments, a map is generated. For example, the map may indicate tissue characterization distribution over space and/or time. Optionally, a map may be generated from generation for each mode and/or from a combination of modes, for example including AEI and UVP. For example, maps may be used interventions. Optionally, a map may be used in a real time while performing an intervention. Data may be processed to indicate a significant condition. For example, the map may indicate tissue type and/or a location of a target for the intervention and/or a status of an intervention. For example, for tissue ablation, a map may be generated indicating tissue viability, and/or lesion status. For example, the map may facilitate assessment of the magnitude of impact of ablation steps. In some embodiments, a map may indicate the effective depth of ablation. For example, the map may be used by an operator and/or an automated procedure to designate a location for further ablation and/or repeated ablation. For example, tissue may be characterized as alive, functioning, moving, contracting, ischemic, edema, scar, necrotic, and the like. For example, tissue may also be characterized by its temperature.

In some embodiments, data may be processed and/or averaged over time, for example over intervals of between 1 to 30 sec. A map is optionally obtained in a gated mode. Optionally, gated mode imaging may provide for clear maps of moving tissue. For example, images of the heart may be combined using cardiac gating. For example, data may be collected separately for separate time slots over the cardiac cycle (e.g. 10-50 time slots, and/or 15-20). Optionally, the time slots may be synchronized to the ECG patterns. For example, information during the systole phase (e.g. during the R-wave) or during the resting phase is collected together to form an image with reduced motion artifacts.

In some embodiments, data is processed by reference values that are either predetermined (e.g. by a look-up table) or pointed by the operator (e.g. by pointing to several regions in the image that are known to be alive, dead, etc.). For example, measured data may be compared to one or more reference values and/or processed with a logical diagnostic algorithm. Processing with reference values is optionally used to indicate levels that are associated with a tissue state. The result is, optionally, presented in real time to the operator (a surgeon, cardiologist, radiologist etc.).

In some embodiments, an imaging method highlights the local electric response and/or conductivity of the tissue being imaged. In some embodiments, the resulting information may be substantially different from the information provided by commonly used imaging methods, such as regular ultrasound imaging or X-ray imaging. In some embodiments, the methodology may be safe. In some embodiments, the methodology may provide high resolution (e.g. millimetric scale or better). In some embodiments, the methodology may be provided in real time (e.g. some macroscopic properties of one points within a region of interest may be obtained updated repeatedly over a time interval of between a fraction of a second and up to tens of seconds. Alternatively or additionally, properties of multiple points obtained within up to tens of milliseconds). In some embodiments, the methodology may be used to indicate tissue anatomy and/or function and/or electrical properties (e.g. function in place of and/or in addition to anatomy). For example, anatomy and/or functioning may be deduced from localized electrical mapping of multiple points within a region of interest.

In some embodiments, a lookup table is used and/or formulas calculated that will include for example thresholds on processed values, e.g. amplitude, frequency response, slew rates, and other matrix or tensor properties (e.g. when measured simultaneously from different orientation, and different polarizations by multiple electrodes or antennas). The estimated properties may be mapped into categories and or color-coded display. Different electrical characteristics may be associated to different tissue states (e.g. for heart tissue refractory, contracting, rest, etc.) and different tissue condition (healthy, edema, necrotic, ischemia, etc.). Optionally, by mapping tissue states over time, the direction, speed and/or path of various processes such as contraction of muscle, excitation of nerve or tissue etc. are mapped. For example, areas that are functioning properly and/or improperly and/or causing problems in transmission may be detected.

A potential application of this imaging method includes, but is not restricted to, imaging of the heart and/or surrounding tissue before, during and after an arrhythmia ablation procedure.

The imaging may be in real-time, (i.e. images may be updated at a rate that is faster than significant changes in a process being evaluated). For example, real time imaging may facilitate guidance of medical treatment equipment or procedure. Alternatively the imaging is semi-real-time (e.g. the updating rate of the imaging is on the same order and/or slower than a process being evaluated, but faster than a procedure being performed; for example too slow to provide the status of a lesion while ablation is occurring, but fast enough to provide a status of the lesion while the operator is still working on the patient for example updating may be over a time period ranging between 10 to 30 seconds and/or 30 to 300 sec. and/or between 300 to 180 sec.), providing insight on the results of a treatment and/or directing the progress of the procedure.

In some embodiments of the present invention, the ultrasonic transducer is non-invasive. Alternatively or additionally, the ultrasonic transducer is semi-invasive (e.g. inserted through the esophagus, trans-luminal, trans-rectal, trans-nasal) and/or fully invasive (e.g. trans-vascular, within a heart chamber, within an organ or other tissue, and/or using a catheter).

In some embodiments, electrodes used to deliver an electrical signal and/or to measure electrical properties may be extra-corporeal, e.g. patch electrodes attached to the patient's body and/or intra-corporeal, e.g. intra-venous and/or as part of a catheter.

For the sake of the current disclosure, the terms transducer, acoustic actuator and ultrasound generator/catheter/system are interchangeable (except where one or more meanings is specifically disclaimed and/or does not make sense in the specific context).Wherever one of the terms is mentioned it to be understood that additionally or alternatively one or more of the other terms can be used in another embodiment of this invention. Similarly, the terms tissue, muscle, organ, and tumor are interchangeable throughout this (except where one or more meanings is specifically disclaimed and/or does not make sense in the specific context). Wherever one term is mentioned it to be understood that additionally or alternatively one or more of the other terms can be used in another embodiment of this invention.

Without limiting the scope of the present invention, the systems, methods and examples hereby describes shall have the meaning as if they are described also for imaging, detecting and or characterizing cancer cells, infection, electrical activity of muscles, arrhythmia, central nerves activity and/or peripheral nerves activity.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In some embodiments of the present invention, a method based on the Acousto-Electric effect is proposed for the tridimensional mapping of the electrical activity in the target tissue and/or the tridimensional assessment of cardiac ablation lesions, during the ablation procedure, which provides localized tridimensional indication on lesion formation. In some embodiments, both methods are based on bio-impedance estimation or other electrical property such as charge, potential, dipole and others.

The Acousto-Electric Effect

Without be limited by a particular explanation or theory, the acousto-electric effect may be conceptualized as a phenomenon of local variation in the electric properties of a material, which results from an acoustic wave propagating through the material. This variation may result from the motion of electric charge carriers, or changes of concentrations thereof, being driven by the acoustic wave. It may occur in solids, liquid solutions, and/or in tissue. For example, ions in the cells may be charge carriers.

Without be limited by a particular explanation or theory, in the Acousto-Electric effect the detected electrical signal may be proportional to the ultrasound signal. For instance in the AEI case the relationship has been formulated as:

$dv = kiR_0 dp$, where dv is the change in detected voltage, i is either a bioelectric current or an induced current, $R_0$ is the electrodes resistance, k is the interaction constant (with units $[Pa^{(-1)}]$) and dp is the change in acoustic pressure.

To the accuracy of the above formulation, a pattern in the input ultrasonic signal may translate into the detected electrical signal (after some distortion, resulting for example from the acoustic propagation in the tissues). Optionally, a system component that is frequency tunable is tuned based on the selected ultrasonic frequency. The tuned component may then be used to receive the signal from the tissue that is currently at the location of the acoustic pulse. Alternatively or additionally, amplitude and/or phase of the acoustic and/or electrical signals may be modified.

In some embodiments, it is possible to determine the location of an acoustic wave at a given time. For example, an acoustic wave may be focused and/or beamed toward a certain location. Alternatively or additionally, propagation velocity of the wave through the tissue may be known. The measured change of electrical properties at a given time may be attributed to the location of the wave at that time and/or to the location of the wave at a known time lag previous to the measurement. The local electric property being affected may include conductivity, charge, potential, dipole and others. The property is optionally measured using one or more set of electrodes in the vicinity of the target, and/or distant from the target. The electrodes are optionally connected to a low noise amplifier. For example, the system may capture variation in the measured dipoles, potentials and/or currents from the tissue. Optionally, a circuitry is used to match and/or correlate and/or apply gating and/or integration and/or other signal processing to measure the electrical property changes with time correlation to the emitted ultrasonic wave passing through the target tissue.

The measured acousto-electric effect may be distinct from acoustic effects usually utilized in echo or Doppler ultrasound imaging. The methodology optionally gives information on the structure and/or function of tissue. In some examples of the present invention, the result of the acousto-electric information is used for diagnosis, for guidance of an intervention, (for example a catheter and/or a treatment). For example the information may be used for lesion assessment as part of an ablation procedure and/or as an add-on to ultrasonic imaging modality or other imaging modalities. For example, a map of tissue may be made including data from ultrasound and/or other imaging modalities and/or information deduced from acousto-electrical measurements. For example, a 2D and/or 3D map may show structure and/or functioning of the tissue together.

Exemplary Acousto-Electric Effect for Mapping/Lesion Assessment

As mentioned above the Acousto-Electric effect is the modulation of electric impedance $\rho$ by acoustic pressure waves. It can be formulated as: $\Delta\rho/\rho_0 = -KP$ where $\Delta\rho$ is the change in impedance, $\rho_0$ is the direct current (DC) impedance, K is a constant of interaction (with units: $Pa^{-1}$) and P is the acoustic pressure.

The total impedance can be developed to: $\rho(x,y,z,t) = \rho_0 - K\rho_0 P$.

In some embodiments, it is assumed a forward facing transducer at the tip of a catheter. In some embodiments, a coordinates system for the ultrasonic transmission from the transducer is generated. For example, the coordinates (x,y) can represent the plane perpendicular to the catheter tip; and the coordinate z is perpendicular to the transducer plane pointing forward from the catheter tip and towards the lesion progression direction.

In some embodiments, a single transducer is located at the catheter tip. In some embodiments, a single forward facing transducer is located at the catheter tip. In some embodiments, a single forward facing transducer with some inclination angle is located at the catheter tip. In some embodiments, multiple transducers are located at the catheter tip, facing forward. In some embodiments, the transducers planes are angled from the tip direction. In some embodiments, the transducers may be mechanically rotated along the catheter main axis in order to measure at an angle to the catheter major axis. In some embodiments, the transducer beam or beams are electronically modified by means of beamforming. In some embodiments, the transducers are perpendicular to the catheter axis, and the ultrasonic beam is directed towards the lesion using an ultrasonic reflector, which is part of the catheter.

In some embodiments, an ultrasonic source, targeted at the lesion site, produces a pressure field P(x,y,z,t) with a central frequency that is set, but is not limited to, the following exemplary values: 500 KHz, 1 MHz, between 1-3 MHz, less than 10 MHz, between 10-30 MHz. In some embodiments, a pair of electrodes induces the target tissue with an alternating current I(t), with a frequency lower than the ultrasonic central frequency, with exemplary values that range between, but are not limited to: 10-100 Hz, between 1-5 KHz, between 1-20 KHz, less than 50 KHz.

In some embodiments, a voltage V(t) is measured by a second pair of electrodes. In some embodiments, the following relation, exist between induced current and measured voltage:

$$V(t) = I(t) \cdot \iiint \rho_0(x,y,z,t)(1-KP(x,y,z,t))dxdydz = V^{LF}(t) + V^{AE}(t)$$

Measured voltage is the sum of a low frequency voltage $V^{LF}(t)$—that is filtered out and a voltage resulting from the Acousto-Electric effect: $V^{AE}(t)$.

In some embodiments, the acoustic pressure field is represented as:

$$P = P_0 b(x, y, z) a\left(t - \frac{z}{c}\right)$$

where b(x,y,z) is the beam pattern, $P_0$ is the amplitude of the pressure pulse and a(t) is the pulse waveform.

In some embodiments, the ultrasonic signal is focused to a focal point with a diameter in the order of 1-2 millimeters. In some embodiments, focusing is achieved using a focused (curved) transducer and/or by a phased array of transducers. In some embodiments, targeting different locations on the surface or in the depth of the lesion site and/or its surrounding is achieved by mechanical movement of a focused transducer and/or by beam steering of a transducer array. In some embodiments, since the area of interest (for mapping and/or ablation) and/or its surrounding is in the order of 3 centimeters, the acoustic pressure distribution—represented by the beam pattern—can be considered as a delta function centered on the focal point with coordinates $(x_1, y_1, d)$, resulting in the following derivation of the a localized impedance estimation:

$$\rho(x_1, y_1, d, t) \cdot P(x_1, y_1, d, t) \approx \tilde{K} \frac{V^{AE}(x_1, y_1, d, t)}{I(t)}$$

Where d is the depth (e.g. distance from transducer plane along the z-axis) at which impedance is estimated, and $V(x_1,y_1,d,t)$ is the measured acousto-electric voltage when the ultrasonic signal is focused on $x_1,y_1$ in the XY plane and d is the depth dimension. In some embodiments, $P(x_1,y_1,d,t)$ is the sampled acoustic pressure field, at the focal point.

It is known in the art that measurements of bio-impedance of the tissue (LBI) are influenced by effects of the acoustic signal propagation through the tissue, which includes, for example, reflections, scattering and absorption, all usually resulting in signal attenuation and interference. In some embodiments, a good estimation of local bio-impedance in various locations and depths during the mapping and/or ablation procedure, enabling frequent updates of estimated values (high refresh rate), while maintaining high estimation signal to noise ratio (SNR), is desired. In some embodiments, in order to achieve this goal, coding schemes for the acoustic signal and decoding methods for the LBI estimation are used (see for example below).

Referring now to FIG. 1, showing a schematic representation of the use of focused ultrasound for the localization of electrical property estimation of the tissue (e.g. impedance, charge, potential) as part of image mapping and/or lesion assessment, during a cardiac ablation procedure.

In some embodiments, a catheter 100 is used carrying either a single ultrasound transducer 102, or an array of transducers, at the tip of the catheter. In some embodiments, two distinct catheters are used, one for anatomical and/or electrical mapping and another for ablation. In some embodiments, a single catheter is used for ablation and for anatomical and/or electrical mapping. In some embodiments, each transducer in the array, functions as an individual focused transducer (by an ultrasonic lense or by having a curved shape), enabling a single or a set of focal points at distant planes. In some embodiments, the transducer array functions as a phased array, creating a focal point using beamforming methods.

In some embodiments, the catheter head is positioned in front of the outer layer of a myocardial tissue 104, where the ablation takes place. 106 illustrates a cross section of the lesion created by the ablation on the outer layer, during the ablation procedure. In some embodiments, ultrasonic signal propagates through the inner layers of the tissue 108, and is focused at a distant inner layer, for the estimation of electrical properties of the target tissue before, during and after the lesion, in depth of the tissue 110 (cross section 112). In some embodiments, an area of interest 114 is defined, in and around the cross section of the target tissue in the depth of the tissue. In some embodiments, ultrasonic beam or beams create focal points 116 defining small regions where electrical properties, such as impedance, are estimated. In some embodiments, regions around the place of the lesion are important for relative comparison of electrical properties.

In some embodiments, the transducer beam is designed to measure in a depth direction. In some embodiments, an ultrasonic pulse propagates along the transducer beam, approximately filling a coin shaped volume at any given point of time In some embodiments, steering of focal point is achieved by mechanism of beam steering (e.g. changing of signal phases to change the direction of the main lobe). In some embodiments, in a single cycle of tissue assessment and/or tissue lesion assessment, the beam is steered to different directions. In some embodiments, in each direction, a sequence of pulses is transmitted and propagated through the tissue. In some embodiments, each pulse estimates, for example, tissue impedance, at a certain depth. In some embodiments, the sequence of pulses maximizes SNR in the estimation given the length of the cycle and required resolution (see next section). In some embodiments, at the end of the cycle, the system has information on all different locations in depth, and assesses the electrical activity in the target tissue and/or the progression of the lesion formation by comparing to the results of previous cycles.

Figure 2:
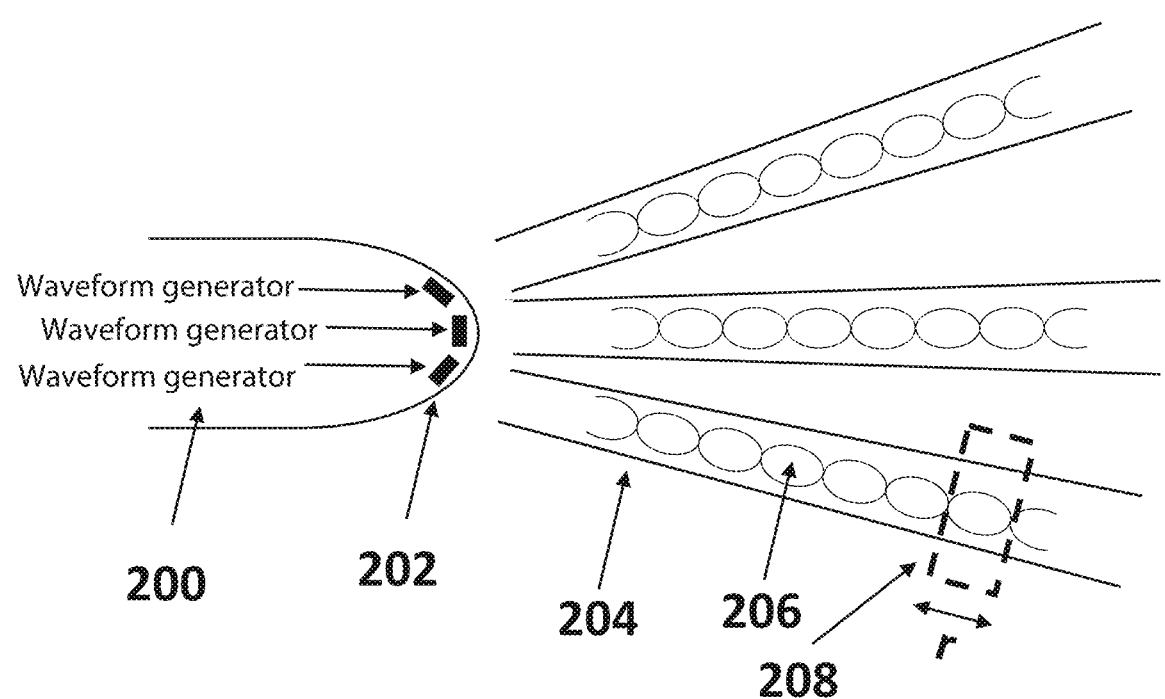
FIG. 2 is a schematic representation of the principle of action of the device, according to some embodiments of the present invention.

Referring now to FIG. 2, showing a schematic representation of the principle of action of the device, according to some embodiments of the present invention. In some embodiments, a catheter 200 comprising forward facing ultrasonic transducers 202, face towards the heart wall. In some embodiments, the transducers are on the same plane. In some embodiments, the transducers form beams using beamforming techniques. In some embodiments, the transducers are placed on a curved plane, such that the angles of the transducers are fanning out, as shown for example, in FIG. 2. In the example shown in in FIG. 2, the beams of three of the transducers are shown. In some embodiments, the beam 204 emitted from the bottom transducer contains a number of packets 206. In some embodiments, each packet 206 is of length r, which is the depth resolution of the system. In some embodiments, the area around the packet 208 is an area from which the LBI is measured. In some embodiments, small movements of the catheter or the heart may move the packet location, and therefore the volume of 208 is larger than the beam. In some embodiments, all the different volumes are simultaneously measured.

Figure 3:
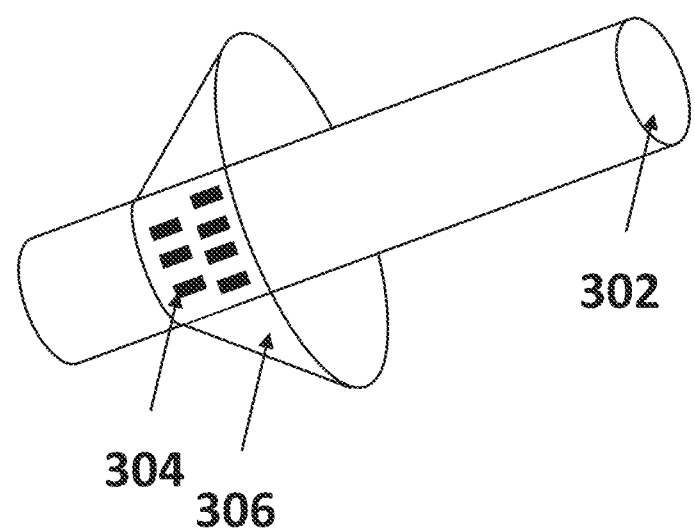
FIG. 3 is a schematic representation of a catheter comprising side-facing transducers, according to some embodiments of the present invention.

Referring now to FIG. 3, showing a schematic representation of a catheter comprising side-facing transducers. In some embodiments, the transducers are not located in the tip of the catheter. In some embodiments, the tip of catheter 302 is used for electrodes that measure, induce current and/or perform lesions. In some embodiments, the tip of the catheter 302 is used for mechanically holding the tip in place. In some embodiments, since the tip of the catheter 302 is occupied with other instruments, the transducers are placed away from the tip, as shown for example in FIG. 3. In some embodiments, the transducers 304 are placed near the face of the catheter perpendicular to the major axis of the catheter. In some embodiments, a reflector 306 redirects the transmitted ultrasonic signal forward. In some embodiments, the reflector is part of the catheter. In some embodiments, the reflector is folded during navigation, and expanded when needed. In some embodiments, the reflector material is acoustically different from blood. In some embodiments, the reflector is made of metal. In some embodiments, the reflector is an inflatable instrument.

In some embodiments, the reflector has a conic shape. In some embodiments, the system comprises a configuration of transducers that generate an ultrasonic cross section with two concentric circles, each containing multiple signals from multiple transducers.

In some embodiments, an ultrasonic pulse is directed towards a volume element that can be described as $vol(x_1, y_1, d_1)$. In some embodiments, at time t, when the ultrasound signal is actually at this volume, the measured voltage and $V(x_1,y_1,d,t)$ are used to derive the required LBI. In some embodiments, the propagation of the acoustic pulse within the tissue is not used for other measurements, and the next measurement takes place when the original pulse decays.

In some embodiments, an ultrasonic pulse is directed towards a volume element that can be described as $Vol(x_1, y_1, d_1)$. However, during the propagation of the pulse within the tissue, at different values of d: namely, $d_1, d_2, d_3 \ldots$ the system takes measurements of the voltage at different times, each representing a measurement of the LBI at a different depth value. In some embodiments, this provides a series of measurements $V(x_1,y_1,d_1,t_1)$, $V(x_1,y_1,d_2,t_2)$, $V(x_1,y_1,d_3,t_3), \ldots$ In some embodiments, this method potentially increases efficiency since for each single transmitted pulse, multiple measurements are performed for multiple depth values, and the time required to measure the electrical activity and/or the lesion in the heart wall is shortened. Furthermore, in some embodiments, since every transmitted pulse is used for multiple measurements, the signal to noise ratio required to achieve good LBI estimation is reached after fewer pulses.

Coding Schemes for Acousto-Electric Based Tissue and/or Lesion Assessment

The previous embodiments described a mechanism where a single pulse is transmitted, and thus the measured voltage at any given time t is related to the location of the acousto-electrical effect at a certain volume where the ultrasonic pulse is concentrated.

In some embodiments, ultrasonic energy is spread over a long period of time and over large volumes that include many areas of interest, and using coding, the contributions from different parts can be separated, identified and analyzed without the problem of mutual interference.

In some embodiments, the system provides measured values of a physiological measure from various locations inside the heart muscle. In some embodiments, coding is used together with an array of transducers, to sample the local bio-impedance (LBI) in a volume. In some embodiments, a single measurement providing estimated LBI values of about 400 different locations takes from about 0.5 miliseconds to about 100 miliseconds. Optionally, from about 1 miliseconds to about 50 miliseconds. Optionally, from about 2 miliseconds to about 20 miliseconds.

Exemplary Assumptions for the Coding Schemes

The bio impedance and the change of bio-impedance over time changes from volume to volume. The typical volume of interest is shaped like a flat disc (coin), with its flat side aligned with the muscle surface, and the narrow side aligned with the depth of the muscle. Such measurement can be achieved, in some embodiments, by a forward looking array of circular transducers facing the chamber wall. Such measurement can be achieved, in some embodiments, by an array of forward looking transducers operating in beamforming.

Figure 4:
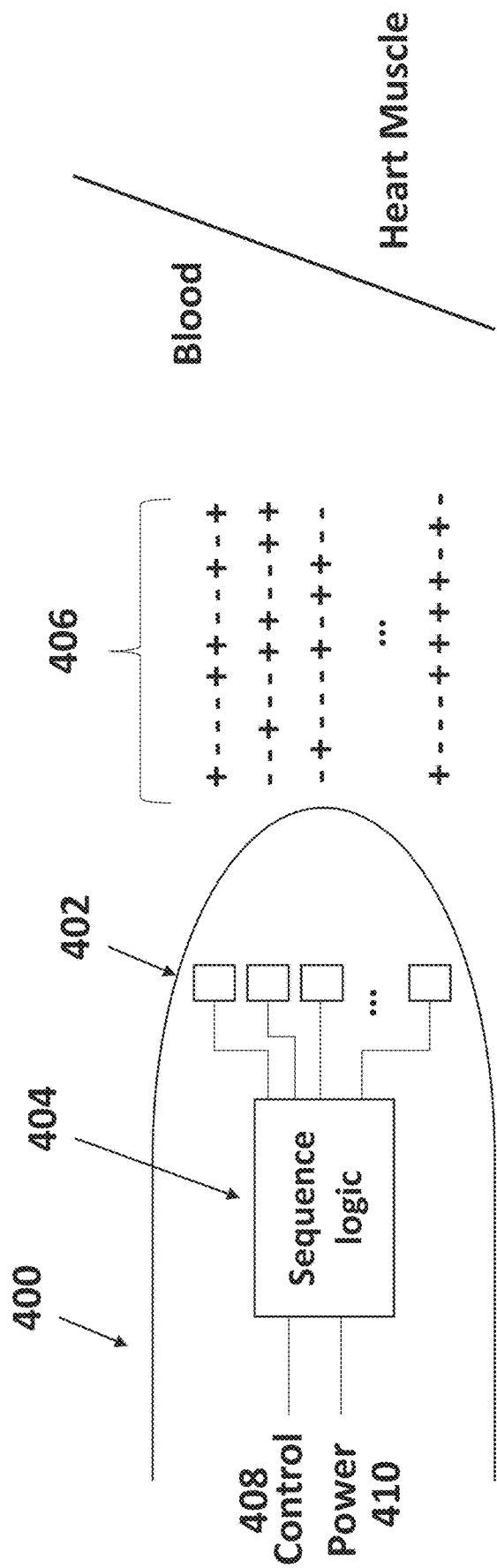
FIG. 4 is a schematic representation of an exemplary implementation of a coded system, according to some embodiments of the present invention.

Referring now to FIG. 4, showing a schematic representation of an exemplary implementation of a coded system. In some embodiments, inside the catheter 400 there are a number of forward facing transducers 402, connected to a sequence logic module 404. In some embodiments, the sequence logic module 404 generates sequences 406 for the transducers 402. In some embodiments, the sequences 406 are time shifts of a single pseudo random sequence (or m-sequence) as detailed herein. In some embodiments, the sequences 406 are taken from a multi-sequence code such as Kasami code, as detailed herein.

In some embodiments, the sequence logic module 404 receives from the base of the catheter 400 a control signal 408 and power 410. Optionally, there is no need to move all the transducer electrical signals on separate leads along the catheter. This potentially simplifies catheter production.

In the figure, the emitted sequences 406 are depicted a sequence of + and − signs. In some embodiments, this means that the basic transmitted pulse that is generated by the transducer is multiplied either by 1 (e.g. no change) or by −1 (e.g. reversed sign). In some embodiments, this feature possibly simplifies the implementation of the electrical circuits inside the tip of the catheter.

In some embodiments, the ultrasonic signal travels through the blood and reaches the heart wall. In some embodiments, the different locations and depths are measured simultaneously.

Exemplary structural parameters for the coding schemes

| Parameter Name | Parameter Meaning | Value | units |
| --- | --- | --- | --- |
| $D_w$ | Depth of heart wall | 20 | mm |
| S | Total area of interest on heart wall | 140 | mm$^2$ |
| $D_b$ | Distance from transducer to heart wall | <30 | mm |

Exemplary Informational parameters
(e.g. what the physician needs to know)

| Parameter Name | Parameter Meaning | Value | Units | comment |
| --- | --- | --- | --- | --- |
| R | Depth Resolution - resolution of interest for volume element (voxel) | 2 | mm | |
| $R_d$ | Radius of interest of volume element | 1-1.5 | mm | Area = 3 − 7 mm$^2$ |
| $D_c$ | Distance between center of adjacent volumes | 2-4 | mm | |
| K | Number of sampled discs per layer | 7-16 | | |

Exemplary Single Transducer Model

In some embodiments, the system comprises a single transducer, as disclosed, for example, in the following paragraphs. In some embodiments, the single transducer model explains the formula derivation as a precursor to a multiple transducer system.

In some embodiments, measurements of different regions of the heart are taken one at a time. In some embodiments, the transducer is directed mechanically to different zones of interest.

Figure 5:
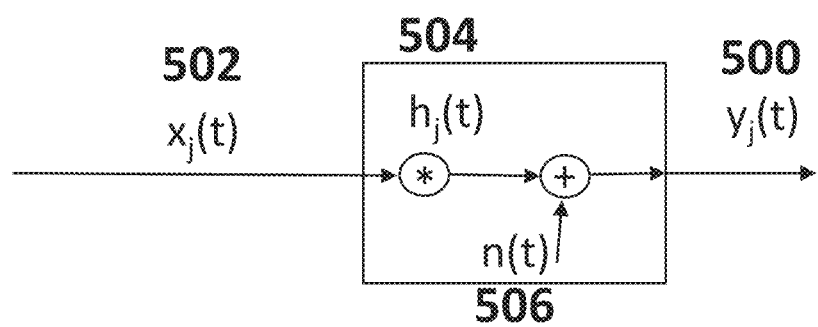
FIG. 5 is a schematic representation of the total transfer function of one transducer, according to some embodiments of the present invention.

In some embodiments, there is a total transfer function, from the pressure at the face of the transducer to the electrical signal at the electrode. In some embodiments, this transfer function includes the cascade of three linear effects:

1. Propagation of the acoustic signal in the body, which includes reflection from discontinuities of the acoustic impedance, and absorption, which is frequency dependent.
2. Acousto electric effect that depends on the acoustic pressure at the tissue, the current flowing through the tissue, and the make of the tissue. These are reflected in the LBI.
3. The local alignment of the current flow vector and the electrical field vector induced by the receiving electrodes Referring now to FIG. 5, showing a schematic representation of the total transfer function with a single transducer. In some embodiments, all together, for a given time and a given location, where the ultrasonic pressure is located, these three functions are summarized in a received signal y(t) (500) that is linearly dependent on the acoustic pressure at the tissue forming the acousto-electric effect. Since it is assumed, in some embodiments, that there is a linear relationship between input and output, the general case to describe it in a time domain is, based on the linear time invariant system theory, a convolution with a function h(t):

$y(t) = x(t)*h(t) + n(t)$ (500) (502) (504) (506)

Or explicitly $$y(t) = \int_{-\infty}^{\infty} x(\tau)h(t-\tau)d\tau + n(t)$$

In some embodiments, the difficulty is estimating h(t) from the known x(t), and measured y(t). For instance, ideally, by transmitting a delta function:

$$x(t) = \begin{cases} \infty & t = 0 \\ 0 & t \neq 0 \end{cases}$$

We would get y(t)=h(t)+n(t).

However, an infinite impulse is impossible to achieve and the transducer is limited in the peak pressure as well as with the finite bandwidth. Assuming a transmission of an as-short-as-possible-as-high-as-possible pulse from the transducer, and the duration that the pulse is different from zero is marked as $T_p$. When the pulse occupies the first voxel adjacent to the transducer's face, due to the acousto-electric coupling, a measure of a y(t), $0<t<T_p$ signal at the electrodes over the short period of time $[0:T_p]$. Next, the acoustic pulse would propagate to the next voxel and a second measure of another signal y(t), $T_p<t<2T_p$. In some embodiments, this measurement depends on the acoustic pressure in the voxel (which already is somewhat lower than the pressure that vibrated the first voxel due to absorption), the local bio-impedance, and the current flowing through this voxel. In some embodiments, this would continue until the pulse exits the area of interest, which is the external wall of the heart.

In some embodiments, it can be seen that while the transmitted acoustic burst traverses the body along its path, the received signal at any given time represents the result of the acousto-electric effect at that volume.

Assuming there is such a short transmission function $a_T(t)$ which defines the pressure output of the transducer for a given short period $0<t<T_p$. Next, assuming the receiver is built with some integration and filtering function $a_R(t)$, followed by a sampling mechanism at points $t=iT_p$, $i>0$; the sampled signal $y[i]$ would be following the receiver function:

$$y_{[i]} = \int_{-\infty}^{\infty} y(\tau) * a_R(t-\tau) d\tau \big|_{t=iT_p}$$

In some embodiments, for a single pulse propagating along the disks we have:

$$y_{[i]} = h_i + n \text{ where } y \text{ is sampled at time } iT_p$$

$h_i$ is the value that corresponds to the location at distance (iR) from the transducer (with r being the distance resolution, that the signal travels during a time period $T_p$).

Exemplary Correction of the Measured Value for Ultrasound Absorption

In some embodiments, in order to get a local measurement value that relates to the LBI in some volume, there is the need to correct $h_i$ with some local coefficients, such as the amplitude decay of the acoustic signal until it reached said volume, and the local current.

In some embodiments, the attenuation and/or correction is determined, for example, by the following rules:
1. There is very low attenuation in blood.
2. At the blood muscle barrier, 7% of the signal shall be reflected. The transmission through the heart muscle is across the fibers. The actual slope of the signal is calibrated. In some embodiments, it is calibrated prior to the usage in operation. In some embodiments, it is calibrated using a receiver transducer that measures the reflected acoustic signal from the tissue.

In some embodiments, the receiving transducer is at the other side of the heart wall, measuring pressure decay along the path from the transmitter to receiver.

Figure 6:
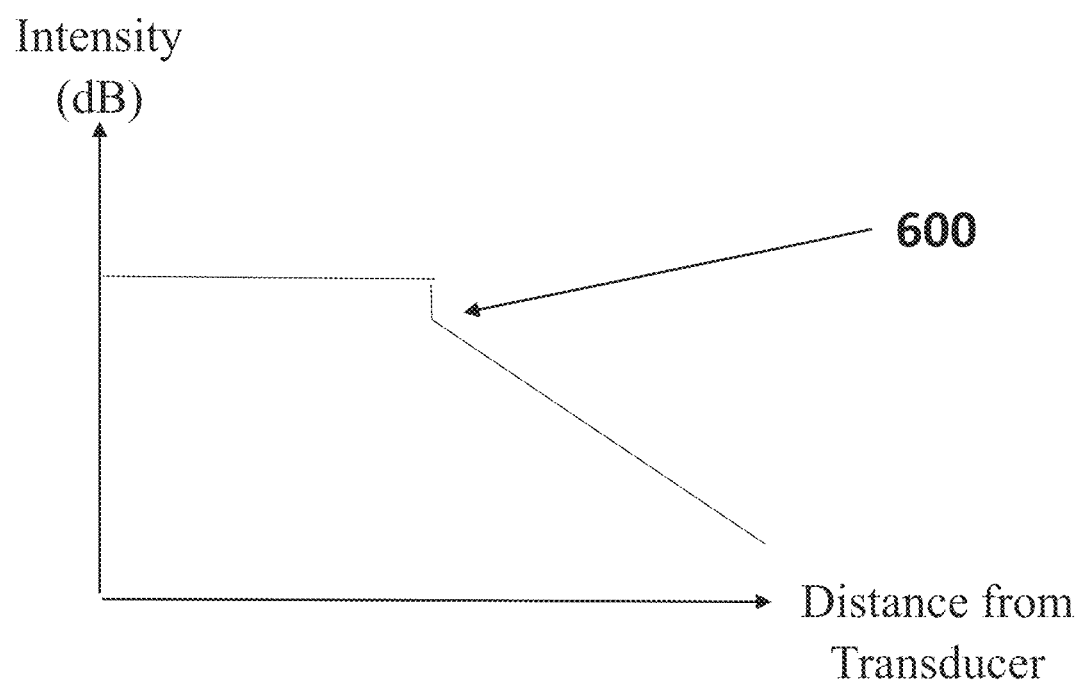
FIG. 6 is a graph of the acoustic wave as it travels from a transducer inside the heart, towards the outer parts of the heart.

In some embodiments, the graph of the log(intensity) is as shown, for example, in FIG. 6. 600 is pointing at the blood muscle barrier. A correction factor W(d) is used to adjust d (an arbitrary distance variable depicting the distance from the transducer face to the volume of interest) so it shall not depend on the ultrasound attenuation.

$$Z_i = \frac{h_i}{W(iR)}$$

Where $Z_i$ is the independent estimation of the LBI, R is the resolution unit and W(d) is the actual attenuation function shown in FIG. 6.

Exemplary Solving the Signal to Noise Problem

In some embodiments, measuring the LBI along the ultrasonic lobe of a single transducer may encounter an estimation problem. In some embodiments, the collected signal is week compared to the additive noise. In some embodiments, in order to solve this problem, more measurements are required.

In some embodiments, coding techniques are employed to improve the signal to noise ratio.

In some embodiments, assuming that instead of transmitting just one ultrasonic symbol, a sequence of symbols is transmitted. In some embodiments, a stream of transmissions multiplied by 1 or by −1. This type of encoding has many names—binary phase shift keying (BPSK) is a term used in communication.

In some embodiments, the transmitted signal is modulated by a sequence of signals m[i], i>0 in such a way that the transmitted signal is:

$$x(t) = \sum_{i=1}^{\infty} m_{[i]} a_T(t - iT)$$

Then, in some embodiments, with a chosen $a_T(t)$ and $a_R(t)$, the system can be described discrete form:

$$y = m * h + n, \text{ or } y_i = \sum_{k=-\infty}^{\infty} h_{[i-k]} m_{[k]} + n_i$$

In some embodiments, $a_T(t)$ uses windowing in the time domain to adjust the pulse shape to the capabilities of the transducer. In some embodiments $a_T(t)$ is determined by the electrical circuit driving the transducer and by the transducer transfer function. In some embodiments, the electrical signal driving the transducer is shaped in order to reduce the overall bandwidth of the signal. In some embodiments, the shaping of the electrical signal uses a window function, such as a raised cosine function. In some embodiments, $a_T(t)$ is implemented using electrical pulse shaping at a high frequency, above the center frequency of the transducer.

The problem stated above resembles the problem of channel estimation in the context of communication systems, with a training signal. In some embodiments, this problem can be stated in matrix form:

$$y = Mh + n$$

Where y is the vector of measurements $y_{[i]}$, the vector h is $h = [h_1, h_2, \ldots h_L]^T$
L is the length of interest, where we want to estimate $h_{[i]}$ values.

$$L = \frac{(D_w + D_b)}{R} = 25$$

N is the length of the sequence $m_{[i]}$. Given the use of cyclical sequences, one may extend the sequence by additional L samples, transmitting $m_{[i]}$, $0<i\leq N+L$ The matrix M is the Toeplitz matrix generated by the transmitted sequence $$M = \begin{bmatrix} m_{[L]} & \cdots & m_{[2]} & m_{[1]} \\ \vdots & \ddots & \vdots & \\ m_{[N+L]} & \cdots & m_{[N+1]} & m_{[N]} \end{bmatrix}$$

In this case, the estimation of the vector h, which is designated as $\hat{h}$ shall be $$\hat{h} = \arg \min_h \|y - Mh\|^2$$

In some conditions, an optimal solution is known to this estimation problem. For instance, if the noise is white Gaussian noise, then the Least Square solution will give the following $$\hat{h}_{LS}=(M^H M)^{-1} M^H y$$

Where $M^H$ represents the Hermitian conjugate of M.
Carefully selected sequences have an attractive $M^H M$ structure, where most of the signal is on the main diagonal of the matrix. If time shifts of the m sequence are orthogonal to itself, then the $M^H M$ matrix becomes an identity matrix. In this case, $M^H M$ is a diagonal matrix, and the receiver becomes very simple to implement—just multiply the input sampled measurements by the transmitted sequence $M^H y$. This simple implementation gives us the optimal estimator of h.
If $M^H M$ is close to diagonal—like in the case of an m-sequence where the off diagonal values are constant but not zero, the approximation is less accurate. However, $(M^H M)^{-1}$ can be approximated to simplify the implementation.
There are many solutions to the problem of selecting the sequence m. One can use m-sequence, then the autocorrelation of the sequence, which determines the content of the $M^H M$ autocorrelation matrix, is:

$$r(i) = 1/N \sum_{j=1}^{N} m_{[j]} m_{[j+i]} = \begin{cases} 1 & i = 0 \\ -1/N & i \neq 0 \end{cases}$$

This would mean a strong main diagonal and a low level off diagonal values, in the autocorrelation matrix.

In some embodiments, other selections of the sequence m can be:
1. Barker Code
2. Linear Feedback Shift Register (LFSR) code
3. Maximal length sequence (MLS)—also called m-sequence
4. A pair of complementary sequences, transmitted one after the other
5. A sequence of real numbers taken from an independent and identical distribution of random numbers—for example Normal, Uniform, Bernoulli.
6. A Gold code.
7. A Kasami code.

In some embodiments, other sets of signals can be selected for transmission that enable pulse compression. In some embodiments, pulse compression techniques enable to transmit long duration signals with short autocorrelation function, enabling the high resolution (in the range defined by R) as required by the application. Examples for relevant pulse compression techniques:
1. Linear Frequency modulation (Linear FM)
2. Linear Frequency modulation (Linear FM) with windowing Exemplary Multiple Transducer Model In some embodiments, the device comprises multiple transducers. In some embodiments, each transducer transmits signal towards a different volume in space. In some embodiments, each transducer signal examines L consecutive discs (coin shaped) and the total system would provide a transfer function as depicted by FIG. 7.

Figure 7:
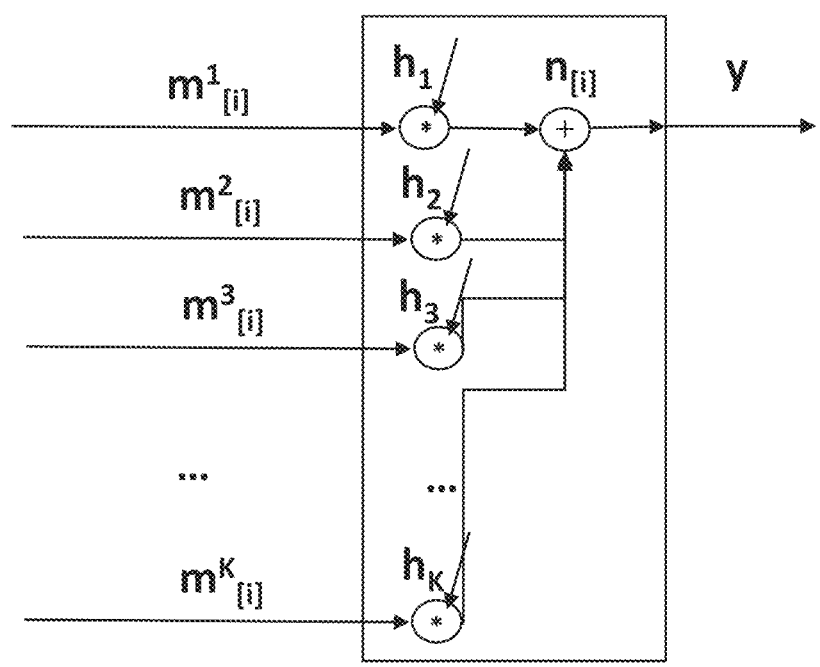
FIG. 7 is a schematic representation of the total transfer function of multiple transducers, according to some embodiments of the present invention.

In FIG. 7, the vector of measurements y remains the same as it was in FIG. 5, but instead of a single sequence transmitted by a single transducer, there are multiple sequences transmitting to multiple transducers.

In this case there is:

$$\tilde{h} = \begin{bmatrix} h_1 \\ \vdots \\ h_K \end{bmatrix}$$

Which is a column vector of length K*L, where
K is the number of transducers
L is the length of interest where h is measured
The matrix M now includes K Toeplitz matrices, one for each transducer $$\tilde{M}=[M_1 M_2 \ldots M_K]$$

Where each individual matrix is the Toeplitz matrix of a single sequence. For sequence j, transmitted at transducer j there is:

$$M_j = \begin{bmatrix} m_{[L]}^j & \cdots & m_{[1]}^j \\ \vdots & \ddots & \vdots \\ m_{[N+L]}^j & \cdots & m_{[N]}^j \end{bmatrix}$$

In matrix form, the estimator given is the same $$\tilde{h}_{LS}=(\tilde{M}^H \tilde{M})^{-1} \tilde{M}^H y$$

Exemplary Sequence Section

In some embodiments, the developed model comprises K sequences. In some embodiments, the quality of the estimation of the vector h depends on the orthogonality of the sequences. In some embodiments, orthogonal set of sequences would provide good estimation.

In some embodiments, for sequence selection, a single m-sequence is used with its advantageous 1/N ratio between the autocorrelation value at zero to the off diagonal values as following.

In some embodiments, the system is designed to measure the LBI simultaneously at a number of different depths (designated by L, as defined above). Since all the different depths are acoustically excited, the measured signal is the sum of all the signals arriving from all excited volume. In some embodiments, the use of coding allows us to estimate the desired values from the measured sum. In some embodiments, the use of orthogonal sequences (where the autocorrelation is 1 for the zero delay and 0 otherwise) allows to estimate the values with no interference between one volume of interest to the other. In some embodiments, the use of an m-sequence is a close approximation of an orthogonal sequence due to its auto correlation function r(i), as stated above.

In some embodiments, the product of the total number of volumes of interest is smaller than the sequence length. In some embodiments, the total number of volumes of interest is the multiplication of the two values K, which is the number of transducers, and L, which is the number of interesting voxels per transducer The formula for this condition is thus:

$$KL < N$$

Example of the Calculations:
The following values form a typical example. The numbers may vary; this example is provided as a demonstration of the calculation only.
Transducer center frequency $F_c$=2 MHz
Speed of sound in tissue c=1500 m/second Required distance resolution (width of the narrow part of the "coin") r=2 mm Maximal Distance from transducer to the distal part of heart wall D=50 mm Number of interesting width volumes L=D/r=25

Number of transducers K=16

Total number of voxels for a single measurement period=KL=16*25=400

Length of time that transducer is stable with relation to heart wall $T_M$=2-100 milliseconds At the given resolution and speed of sound, the time for the single pulse is $T_p$=r/c=0.0013 millisecond. This is the time for a single transducer pulse. In some embodiments, it is assumed that some shaping takes place, extending from the minimal pulse possible as transmitted by the transducer.

In some embodiments, the number of elements in sequence is N=$T_M/T_p$, thus possible value are 1,500<N<76,000.

Examples of Using an m-Sequence Generated by an LFSR Code

1. LFSR of Size 14 Bits, Length 16383

In some embodiments, a maximal length sequence (MLS) (also called m-sequence) is used, which is a linear feedback shift register sequence, or a maximal length ideal sequence with an ideal autocorrelation. For example:

n=14 length of LFSR

N=$2^n$−1=16383 sequence length $m_{[i]}$, i=1 ... N sequence elements, m∈{1, −1}

$$r_{[i]} = \frac{1}{N}\sum_{j=1}^{N} m_{[j]} m_{[j+i]} = \begin{cases} 1 & i = 0 \\ -1/N & i = 1 \ldots (N-1) \end{cases}$$

In some embodiments, it has been seen that KL product was 400. Dividing the m sequence to L almost equal sections. Each section will be Q=round(N/K)=1024 symbols long.

For simplicity, let us assume that $m_s$ is the LFSR sequence, with a defined seed. Then the elements of this sequence are $m_{s[i]}$ i<0<N For each transducer j, j=1 ... 16, the sequence used by this transducer shall be $$m^j = [m_{s[Q(j-1)]}, m_{s[Q(j-1)+1]}, \ldots, m_{s[Q(j-1)+(N+L)]}]$$

given the cyclical extension of the sequence. The cross correlation of this sequence with the original sequence $m_s$ is $$r_{c[i]} = \frac{1}{N}\sum_{j=1}^{N} m_{[j]} m_{[j+i]} = \begin{cases} 1 & i = 0 \\ -1/N & i = 1 \ldots (N-1) \end{cases}$$

In some embodiments, transducer 1 transmits the sequence $m_s$. In some embodiments, any other transducer transmit the sequence $m_j$, and the cross correlation between any two is guaranteed not to show up in any significant value up to a delay of Q.

In some embodiments, at the delay of Q, the amplitude of the acoustic signal is already decayed by a time of $QT_p$=1024*1.3*$10^{-3}$=1.3 milliseconds. In some embodiments, at this delay, the distance travelled by the ultrasound signal is $c*QT_p$≈200 cm. In some embodiments, the signal is decayed in the body at 0.3 dB/cm/MHz, which at 195 cm will give 120 dB. In some embodiments, at this attenuation, no practical interference will remain, and it is completely safe.

In summary, this example shows the use of a single m-sequence with gain of N=16383 or 20*$\log_{10}$(N)=84 dB compared to a single pulse. In some embodiments, the integration period is $N*T_p$=21 milliseconds. In some embodiments, interference from other sequences or other delays is guaranteed to be lower than 64 dB.

2. LFSR of Size 12 Bits, Length 4095

In some embodiments, a maximal length sequence (MLS) (also called m-sequence) is used, which is a linear feedback shift register sequence, or a maximal length ideal sequence with an ideal autocorrelation. For example:

n=12 length of LFSR

N=$2^n$−1=4095 sequence length

Dividing the m-sequence to L almost equal sections, each section will be Q=round(N/K)=256 symbols long.

In some embodiments, using the same scheme as above, the distance that the ultrasound travels before hitting a high value in the correlation matrix would be 50 cm.

In some embodiments, bipolar electrodes are placed near the heart, in a configuration where any signal outside of the volume defined by the electrodes are eliminated from the measurement. In this case, after 50 cm of travel, no acoustic energy will interfere with the measurement.

In some embodiments, the system provides a gain of 20 log 10(4095)=72 dB, with very low interferences from the other sequences.

In some embodiments, different sequences are selected for different transducers. In some embodiments, there is a limitation to cross correlation function between any two transducers at all delays.

In some embodiments, since the number of transducers is small, a small-set Kasami code would fit the problem. For example, for the parameters listed above, the number of sequences in the small-set is N=$2^{n/2}$−1=63, which is above of what is needed for 16 transducers. In some embodiments, from the 63 sequences, the ones with the more attractive cross correlation parameters are selected. For example, an attractive sequence is a sequence with a low maximal absolute value of the cross correlation function to all other selected sequences. In some embodiments the set of 16 sequences (out of the total 63) that has the lowest maximal absolute value of cross correlation between them, is the optimal set, since it provides the maximal signal to interference ratio. Unlike the original m-sequence, the cross correlation will be up to $\sqrt{N}$=64.

$$r_{c[i]} = \frac{1}{N}\sum_{j=1}^{N} m_{[j]} m_{[j+1]} = \begin{cases} 1 & i = Q(j-1) \\ < \sqrt{N} & \text{otherwise} \end{cases}$$

Which gives a coding gain to interference of 20 $\log_{10}$(64) =36 dB.

Exemplary Mapping Imaging System and General Methods

In some embodiments, a desired high spatial resolution imaging (e.g. millimetric resolution or better) is achieved using an ultrasound signal that is temporally short, and/or has short distinctive temporal features (e.g. 1 microsecond or shorter). In some embodiments, the relation between the spatial resolution and the time length of the pulse are related to the speed of sound. In some embodiments, the speed of sound is approximated to 1500 m/s in water. In some embodiments, a more precise value of the speed of sound is used for calculations. In some embodiments, the speed of sound may have a known relationship to the medium through which is it passing and/or may be calculated.

Figure 8:
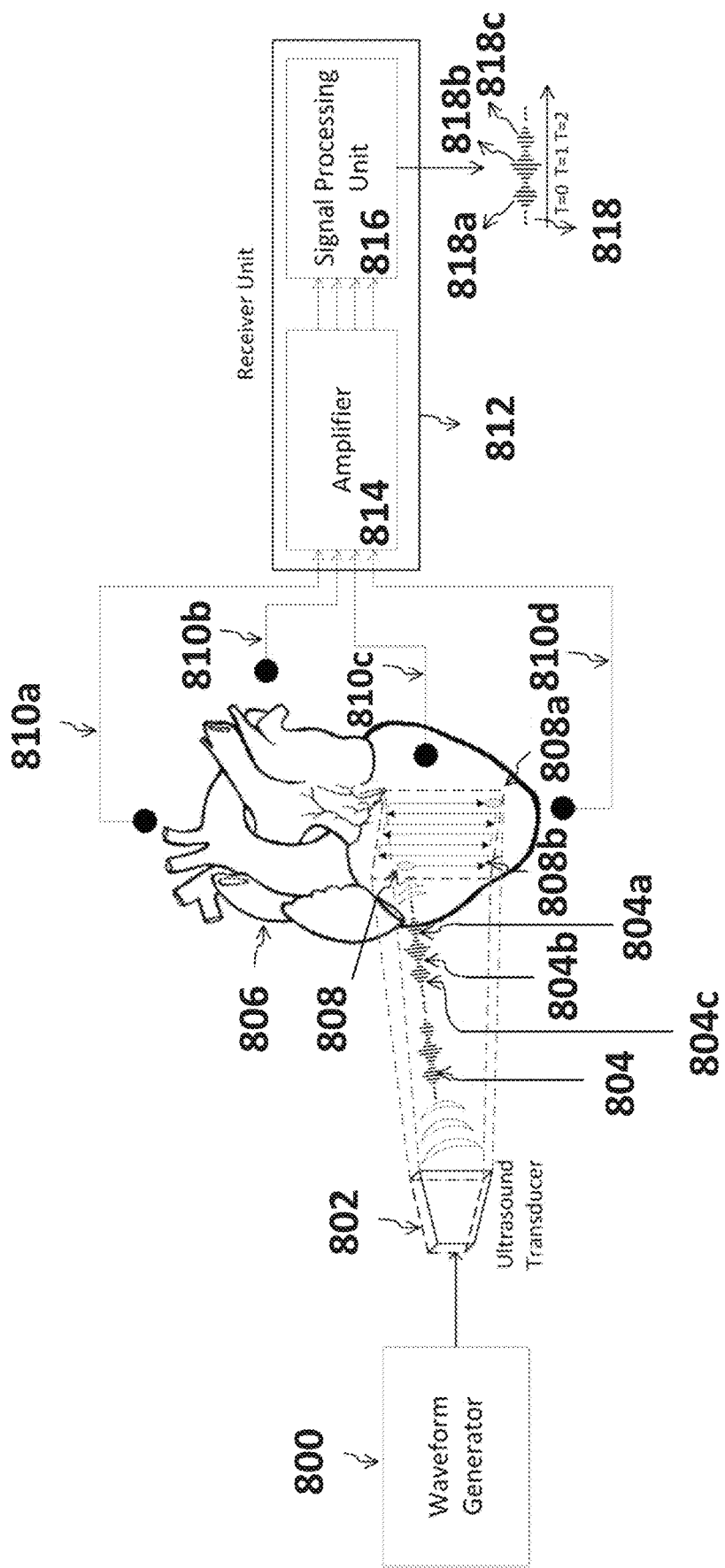
FIG. 8 is a schematic representation of the electronic and physical system, which includes receiving electrodes, according to some embodiments of the present invention.

Referring now to FIG. 8, showing a schematic representation of the system and method of the mapping system. In some embodiments, an acoustic waveform controller 800 generates an output signal that drives an ultrasound transducer 802. In some embodiments, transducer 802 is optionally acoustically coupled to the tissue and/or to the body. In some embodiments, transducer 802 optionally generates an acoustic waveform 804 that travels, optionally in a focused manner, towards the target portion of the tissue 806. In some embodiments, the target tissue is a heart tissue 806. In some embodiments, the waveform 804 includes a pattern with one or more components, for example 804*a* followed by 804*b* and 804*c*. In some embodiments, the ultrasound transducer 802 creates a beam of acoustic energy that is focused on a focal point and/or a focused direction within the target tissue 808. In some embodiments, the beam direction is controlled to scan a region and/or a surface in the target tissue 808*a*, by a selected scanning pattern 808*b*.

In some embodiments, a set of one or more of electrodes 810*a-d* sense an electrical signal (for example the UVP signal produced by the acoustic energy and/or the AEI signal produced by the interaction between the acoustic energy and bio-electric currents in the target tissue). In some embodiments, sensing is monopolar (e.g. relative to a far reference), bipolar (between a pair of electrodes), or a combination of multiple poles. In some embodiments, the one or more electrodes are designed and/or configured to act as antennae suitable for the frequency ranges, with RF properties and coupling suitable for the received signals. In some embodiments, the set of one or more electrodes (or antennas) is positioned in one or more orientations or axes relative to the target portion 808*a* of the tissue 808. In some embodiments, the sensing electrodes are positioned inside the body, for example within the torso, or in proximity to the heart, or in direct contact with the heart, or in the blood, or in a blood vessel (trans vascular), or within the one or more of the heart chambers, or in direct contact with the epicardium or in direct contact of the endocardium, for example on the a free wall or on a septal tissue. In some embodiments, the sensing electrodes are positioned outside the body.

In some embodiments, the set of electrodes are connected to a Receiver Unit 812, which amplifies (by an amplifier 814) and processes (by a Signal Processing Unit 816) the received signals. In some embodiments, the Signal Processing Unit 816 in the Receiver Unit 812 includes one or more of filtering, noise reduction, shaping, matching, gating, equalization, correlation with the generated ultrasonic signal, motion compensation. In some embodiments, they may be electronic hardware, programmable hardware (e.g. FPGA), embedded software or application software. In some embodiments, the Signal Processing Unit 816 depicts electrical variations 818, which correspond to the acoustic wave impact on the target tissue, as denoted in 818*a-c*. In some embodiments, those detected variations can generate information indicative of tissue properties, either as values, 2D maps, 3D maps, superimposed on an anatomical map, etc. In some embodiments, different features of the receiver unit are employed in the generation of a processed image, for example, motion compensation techniques may include gating and/or motion tracking.

Figure 9:
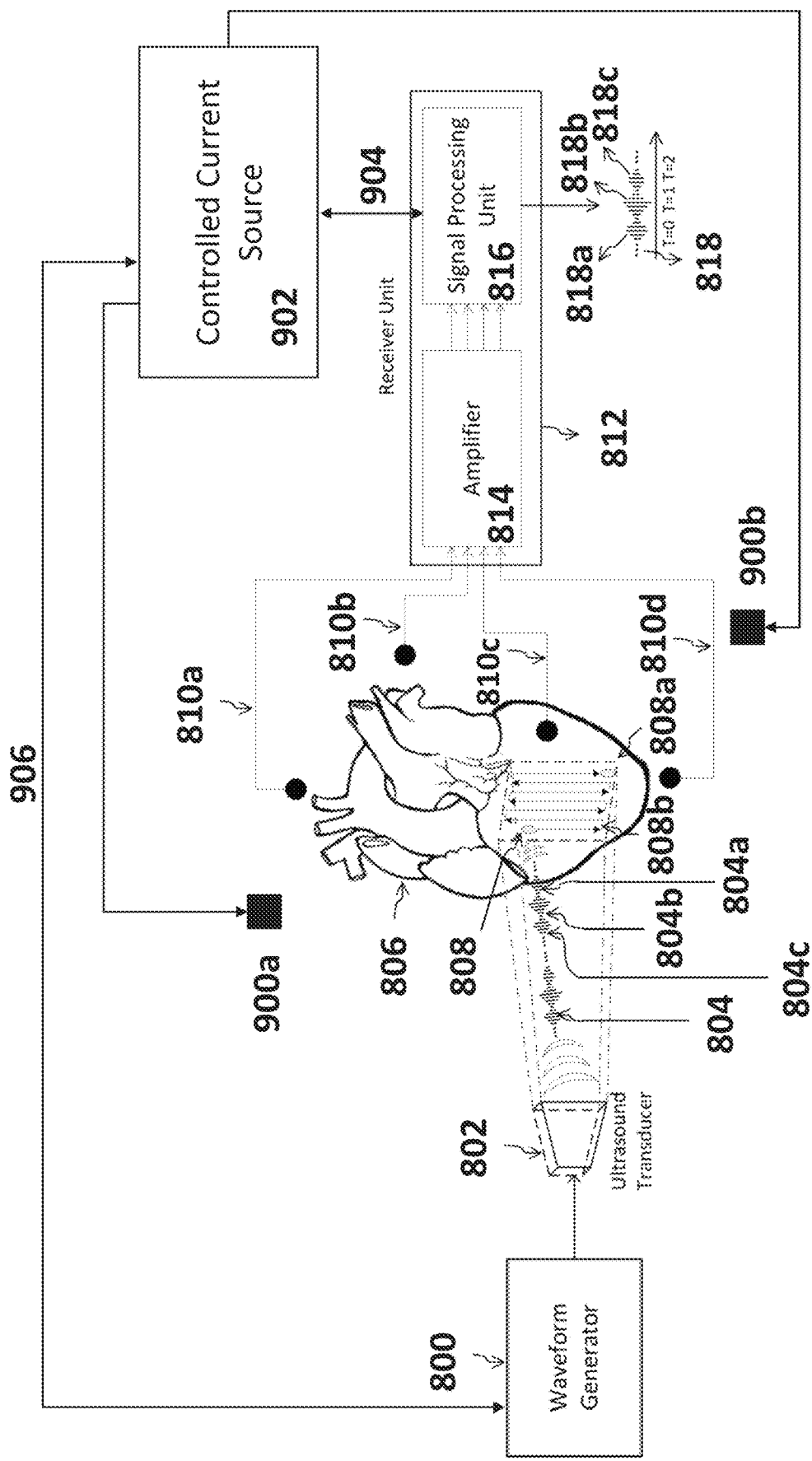
FIG. 9 is a schematic representation of the electronic and physical system, which includes receiving and transmitting electrodes, according to some embodiments of the present invention.

Referring now to FIG. 9 showing an example of some embodiments of the present invention, in which AEI signal is produced by the interaction between the ultrasonic wave and an induced current. In some embodiments, the system includes, in addition to the sensing electrodes 810*a-d*, a set of transmitting electrodes 900*a-b*, and/or possibly more. In some embodiments, the electrodes are connected to a controlled current source 902. In some embodiments, electrical signal delivery is synchronized with tissue activity. For example, synchronization may be through an interface 904 to the Signal Processing Unit 906 in the receiver unit 812, and/or to an ECG device measurement (not shown). In some embodiments, electrical signal delivery is synchronized, for example through an interface 906, with the ultrasonic waveform generation 800.

Figure 10:
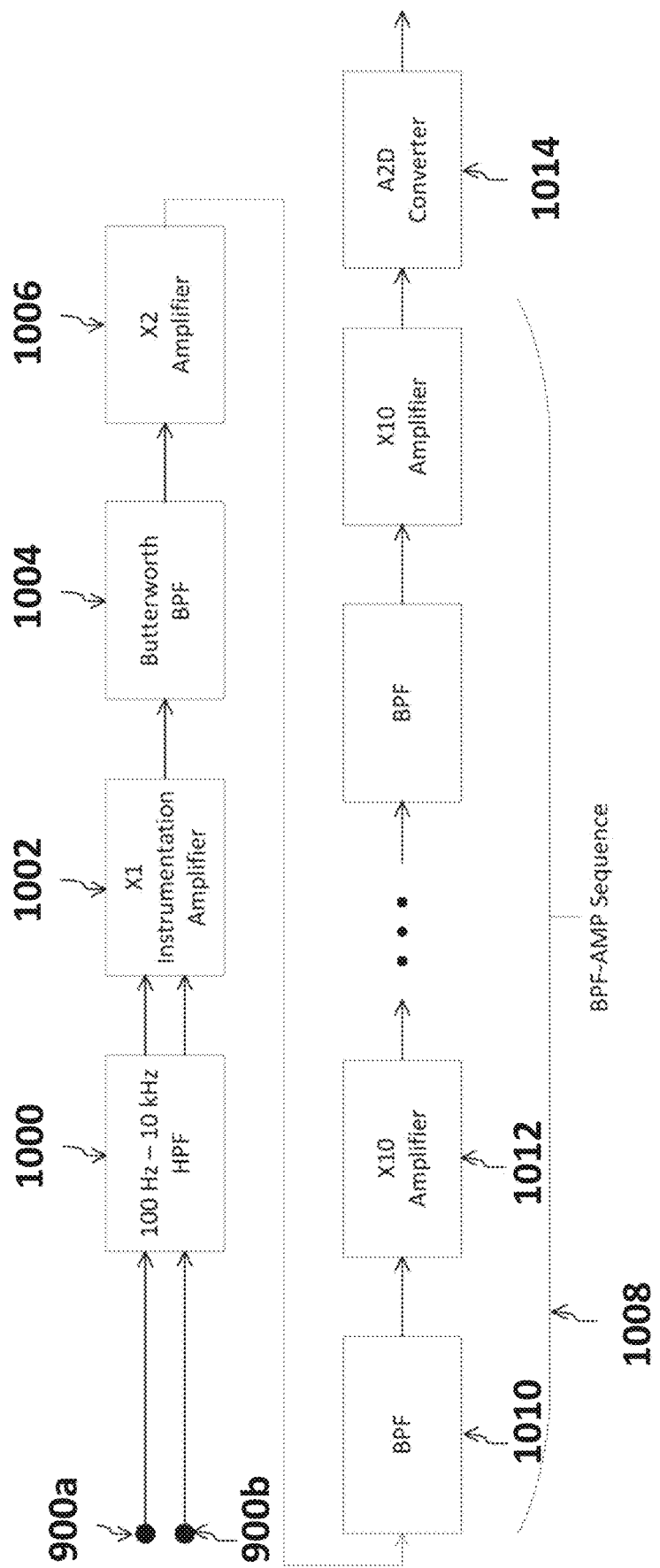
FIG. 10 is a schematic representation of an example of a differential amplification process performed in the amplification unit (amplifier), according to some embodiments of the present invention.

Referring now to FIG. 10, showing a schematic representation of an example of a differential amplification process performed in the amplification unit (amplifier) 814. In some embodiments, the amplification unit is included in the receiver unit 812, for example, as shown in FIGS. 8 and 9. In some embodiments, the amplification unit is a standalone unit. In some embodiments, electrodes 900*a* and 900*b* pick up the electrical signal generated in the target by the Acousto-Electric effect. In some embodiments, for example, the electric signal may be of order ranging between 10 micro-Volts to 1 micro-Volt. In some embodiments, the signal is amplified before sampling, digitizing and/or processing. For example, amplification may be by a factor ranging between about 100 to about 500. Optionally, between about 500 to about 2000. Optionally, between 2000 to 10000. In some embodiments, sensing is mono-polar, where one of the two electrodes is a sensing electrode and the other serves as a reference. In some embodiments, sensing is bi-polar and two electrodes are sensing electrodes. In some embodiments, there are more than two sensing electrodes and the presented amplification scheme is optionally duplicated, for example to filter and/or amplify the sensed signals. In some embodiments, signals are optionally processed differentially (in pairs) and/or individually, relative to a reference.

In some embodiments, a multi-stage amplifier achieves amplification. Optionally, filters are provided between the stages. For example, the filters may keep low noise levels and/or allow further amplification without saturating the next stage. In some embodiments, the first stage of the amplifier functions as a buffer, to increase signal drive strength and/or optimize the CMR (Common Mode Rejection) of the circuit. In some embodiments, the first stage optionally includes a High Pass Filter (HPF) 1000. In some embodiments, the Acousto-Electric signal is proportional to the ultrasound pressure field. For example, relevant information may be contained within frequencies around and/or higher than the ultrasound frequency. Hence, a cutoff frequency of the HPF may be chosen in accordance with the ultrasound frequency. In some embodiments, common mode noise is a significant noise source. Optionally, in the first amplification stage, the HPF is followed by an Instrumentation Amplifier 1002, which performs differential amplification, while maintaining CMRR (Common Mode Rejection Ratio) of −60 dB or better.

In some embodiments, the second amplification stage contains a Butterworth Band Pass Filter (BPF) 1004. For example, the BPF may be chosen to reduce phase distortion in the signal. Optionally, the BPF is followed by a low gain amplifier 164. For example, the gain of amplifier 1006 is chosen to be low enough not to saturate the next stage.

In some embodiments, the next stage is a sequence 1008 of pair of BPFs 1010 and Amplifiers 1012. In some embodiments, the length of sequence 1008 (e.g. the number of blocks) is optionally chosen to achieve the total gain desired. In some embodiments, the total gain is determined according to the gain level to which the digital electronic circuit is sensitive.

In some embodiments, the final stage is an Analog to Digital Converter 1014. For example, the signal is the output of the amplification stage and/or is in the order of 1 millivolt. It has been seen during practical experimentations that the noise at this stage is in the order of 1 Volt. Optionally, sampling depth of the A2D is selected to be 10 bits or more (for example, to allow 1 binary digit to measure the signal). Preferably a 12 bit sampling depth of the A2D is selected (e.g. to allow 3 binary digits to measure the signal) and more preferably 14-16 bits.

In some embodiments, the length of the transmitted signal may be affected by secondary propagation paths. In some embodiments, a secondary signal may interfere with the main transmitted signal and/or add noise to measurements. In some embodiments, the main transmitted signal is distinguished from the secondary signals, for example, according to the time of propagation.

Figure 11:
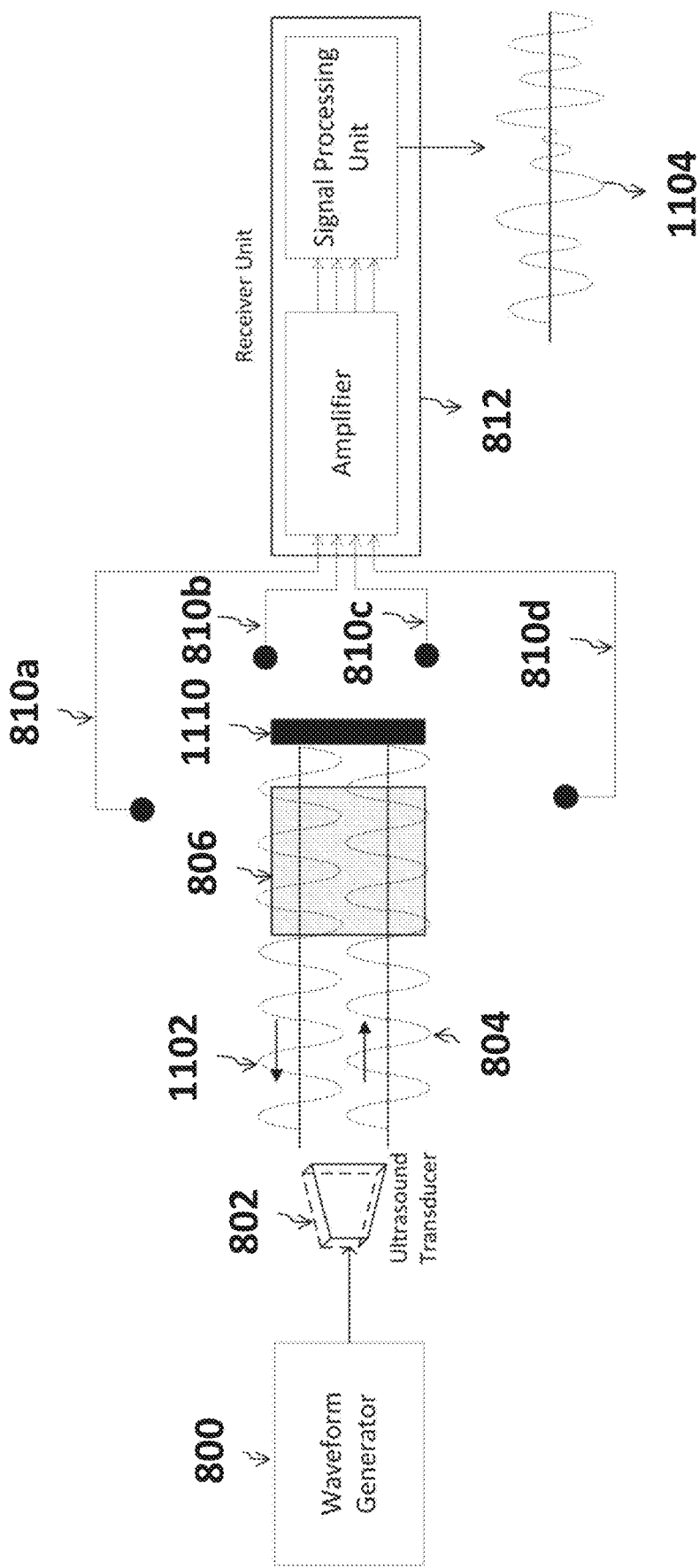
FIG. 11 is a schematic of an exemplary generation of the acoustic waveform, according to some embodiments of the present invention.

Referring now to FIG. 11, showing an exemplary generation of the acoustic waveform, according to some embodiments of the present invention. In some embodiments, the acoustic waveform is generated as shown, for example, in FIG. 11. In some embodiments, the acoustic waveform of FIG. 11 differs from the waveform of FIG. 8, for example, in the signal length. For example, the waveform shown in FIG. 11 may be over 100 microseconds long. Optionally, the waveform comprises identical parts 804*a-c* as shown in FIG. 8.

In some embodiments, the acoustic waveform, passes through the tissue 136 and/or is reflected off a surface and/or an interface 1100 (which may include, for example bone, an air cavity, and others). In some embodiments, the reflected wave 1102 interferes with the incoming wave 804, possibly disrupting the measurement of the properties of tissue 806, the results of this disruption is optionally apparent in the resulting electric signal 1104.

In some embodiments, the recorded signal is weak and/or noisy. In some embodiments, to extract significant data from the signal, the signal is integrated over multiple data points. For example, integration may average out the noise and improve the Signal to Noise Ratio (SNR). In some embodiments, shortening the signal may reduce the number of data points available for integration.

In some embodiments, an ultrasound waveform with a designed pattern is propagated through the target. Optionally, the designated pattern facilitates application of the waveform for an extended time (which may be divided for example into multiple periods) (for example the total time may range between a few microseconds and/or up to several seconds), while facilitating extraction of multiple data points and/or high resolution spatial data from the received signal.

In some embodiments, a chirp waveform is used. A chirp is an example of an ultrasound single with a pattern. In some embodiments, other waveform patterns are possible. For example, in a "chirp" waveform (also known as a sweep signal) the frequency may increase over time. In some embodiments, a linear FM signal is used. In some embodiments, an orthogonal code is used, such as a Costas code. In some embodiments, a patterned waveform activates a medium, through the acousto-electric effect, to produce a similar patterned acousto-electric effect. In some embodiments, changes in the acousto-optical effect, resulting from changes in the pattern of the waveform, are optionally detected. For example, changes in the waveform are optionally patterned to produce a detectible change in the acousto-electrical effect over a time of about 1 microsecond (for example ranging between 0.1 to 0.5 and/or 0.5 to 0.5 and/or between 1.5 to 3 and/or between 3 to 6 and/or between 6 to 20 and/or between 20 to 100 microseconds). In some embodiments, the changes in the acousto-optical effect, resulting from the changes in the waveform pattern, are optionally used as a short feature to provide the desired spatial resolution. In some embodiments, as the transmitted waveform continues, an acousto-electrical signal effect resulting from a different pattern element (for example frequency of wave) is detected for the same portion of the target space. In some embodiments, as the properties of the patterned waveform are known, a series of measurements of acousto-electric effects, resulting from the different frequencies (hence different times), are optionally assembled and/or integrated in a manner that results in minimal noise. In some embodiments, the differentiation between effects of different parts of the pattern facilitates integration of the acousto-electric signal with reduced noise from other propagation paths of the transmitted wave (e.g. echoes).

Figure 12:
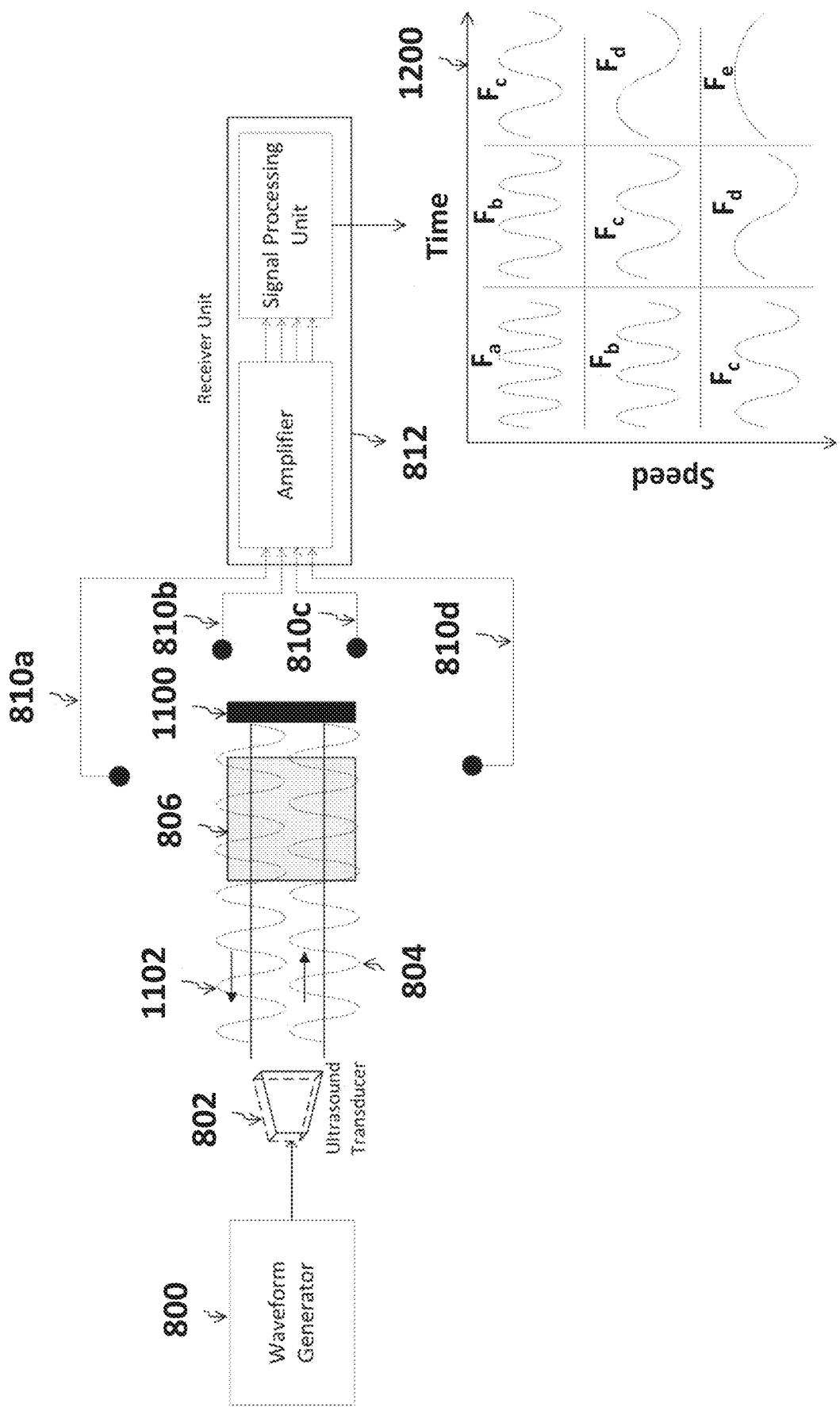
FIG. 12 is a schematic of another exemplary generation of the acoustic waveforms, where different frequencies are transmitted at different times, according to some embodiments of the present invention.

Referring now to FIG. 12, showing another exemplary generation of the acoustic waveform, according to some embodiments of the present invention. As described above, the generation of the waveform is generated as shown in FIG. 11. In some embodiments, the signal frequency in waveform 804 varies linearly and/or in a periodic manner, over time (e.g. the waveform is a 'chirp' signal). In some embodiments the frequency, amplitude and/or phase vary in time in a different manner. For example, in a chirp signal the frequency increases linearly in time, as stated. There can be different variations in the waveform, such as any scheme of digital or analog modulation of the main signal ("carrier wave").

In some embodiments, a tissue at a given location 806 interacts with a different frequency at each moment. In some embodiments, a signal following a different path (e.g. reflected off surface/interface 1110) will present a different frequency component at that time.

In some embodiments, the table of waveforms 1200 shows an example for the direct path component at different times, and at different locations in space. In some embodiments, at any given moment, each location (or propagation path) contributes a different frequency component, relative to the distance traveled by the waveform before interacting with tissue 806.

In some embodiments, the signal picked up by one or more sets of electrodes (for example 810*a-d*) includes different components from the sum of all coincident signal paths. Optionally, one frequency component is contributed predominantly by the direct path. Optionally, using the original waveform 804 as reference, the correct frequency is isolated at each moment. Optionally, each frequency component is short in time. In some embodiments, the short temporal components are optionally used to provide detailed information in high resolution on the tissue 806. Optionally the correct components at each time are integrated over time to improve the SNR. For example, with the improved SNR, more detailed information can be extracted.

In some embodiments, a chirp waveform (and/or another form of coded signal and/or a signal having a sharp "delta-like" auto-correlation, and/or random sequences of signal variation) allows the transmission of a long vibrational signal, while also allowing for correct integration of multiple data points. This optionally provides both a high signal-to-noise ratio, and a high spatial resolution.

Exemplary Visualization of Measured Data for Tissue Assessment

In some embodiments, the system provides three-dimensional data, were the voxel (volume cell) in space is represented independently from the surrounding voxels.

In some embodiments, three-dimensional data is presented as a two-dimensional image on a screen. In some embodiments, the image presented to the user may be of a partial section of the heart or all of it. Optionally, according to the choosing of the user. In some embodiments, the image is a mapping of a three-dimensional manifold onto a flat two-dimensional plane, or displayed in perspective, isometric or free-rotation three-dimensional rendering on the screen.

In some embodiments, the system comprises a plurality of display options for the tissue information. For example, the tissue information can be displayed as a single layer, as a collection of layers, as layer-by-layer scrolling, as partially transparent layers that show simultaneously superimposed layers. Also, for example, as a composition of layers, where the transparency of a layer at a certain location is determined as a function of the values (possibly with a predefined or selectable threshold) in that layer and at that location. Also, for example, as a composition of layers where the values displayed in a certain location is a function of the values in multiple layers across different depths from that location (possibly with a predefined or selectable threshold).

In some embodiments, the system utilizes one or more of the following tools to create meaningful and informational representations of the measured data, possibly providing novel information supporting tissue assessment in cardiac ablation procedures.

In some embodiments, the system utilizes one or more of a (possibly piecewise) polygonal or curved manifold that anatomically substantially corresponds (in most of its control points, e.g. up to an accuracy of about 1, 2, or 3 mm) to the endocardium and/or the epicardium and/or an intermediate layer and/or an artificial layer within the heart chamber and/or an artificial layer outside the heart chamber.

In some embodiments, each manifold corresponds to a fixed thickness in mm, for example each manifold represents a real-world layer 1-10 mm thick, for example 5 mm thick.

In some embodiments, each manifold may represent a varying thickness, different between manifolds and even within the same manifold, so that the entire heart is divided into a fixed (and possibly configurable) number of complete manifolds. In areas where the heart wall is thicker, each manifold represents a thicker layer.

In some embodiments, the system utilizes one or more of a (possibly piecewise) planar, and/or polygonal and/or curved manifold that represents a virtual shape, e.g. spherical, ellipsoid, cylindrical, and/or parts and/or planar and/or combinations thereof, which anatomically substantially corresponds (in most of its control points, e.g. up to an accuracy of about 1, 2, or 3 mm) to the endocardium and/or the epicardium and/or an intermediate layer and/or an artificial layer within the heart chamber and/or an artificial layer outside the heart chamber.

In some embodiments, for example, the system displays in a more transparent manner for voxels representing tissue that is dead as compared with voxels (e.g. deeper voxels) with tissue that is more alive and pulsatile and or at edema state.

In some embodiments, the displayed voxel is fully transparent if it has a value below or above a threshold (fixed or configurable). In some embodiments, the level of transparency is proportional to the voxel's value.

In some embodiments, for example, the system displays a score that corresponds to the maximal and/or minimal viability and/or activity across multiple depths from a certain location.

In some embodiments, for example, the system displays the gradient values of the original data, providing an image of the spatial change in the voxel space. In some embodiments, this type of image may assist differentiating between various parts or regions of the heart (as edges and borders between different regions are highlighted).

In some embodiments, for example, the system displays an image of the difference between two sets of data recorded in two different times, either sequential or some time apart. In some embodiments, this type of image highlights the result of actions taken during the procedure (e.g. ablation procedure), by removing all of the data that is unchanged between the two sets of measurements.

In some embodiments, the system provides the information similar to that of a CT/MR imaging. For example, as an XYZ presentation (in selected orientations of the slices) with scrolling through the X, Y or Z-axis.

Figure 13:
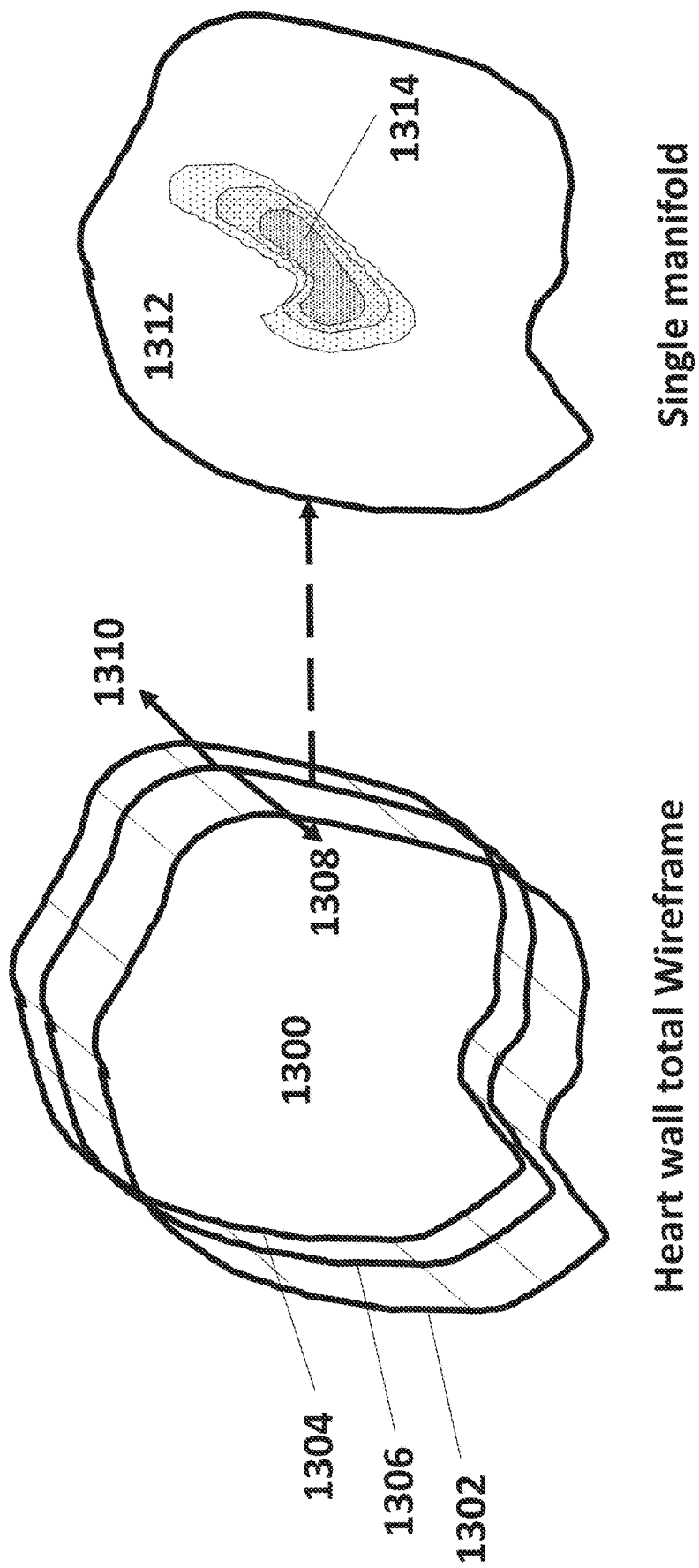
FIG. 13 is a schematic representation of an exemplary visualization technique, where the heart is visualized as a series of flat slides.

Referring now to FIG. 13, showing a schematic representation of an exemplary visualization technique. The Figure shows a wireframe of the heart wall section 1300. In this example there are three manifolds shown—the inner manifold 1302, the outer manifold 1304 and an arbitrary intermediate manifold of interest 1306. In some embodiments, the user may move the manifold of interest towards the outer surface of the heart wall—depicted in arrow 1308—or towards the inner part of the heart—as depicted in arrow 1310. In some embodiments, the selected manifold is copied on the right hand side of the display 1312. An example of a designated function is shown as a color map 1314 on the manifold. In this example, the color corresponds to an estimated function showing the necrosis of the tissue. The darker color at the center describes a higher degree of necrosis.

Figure 14:
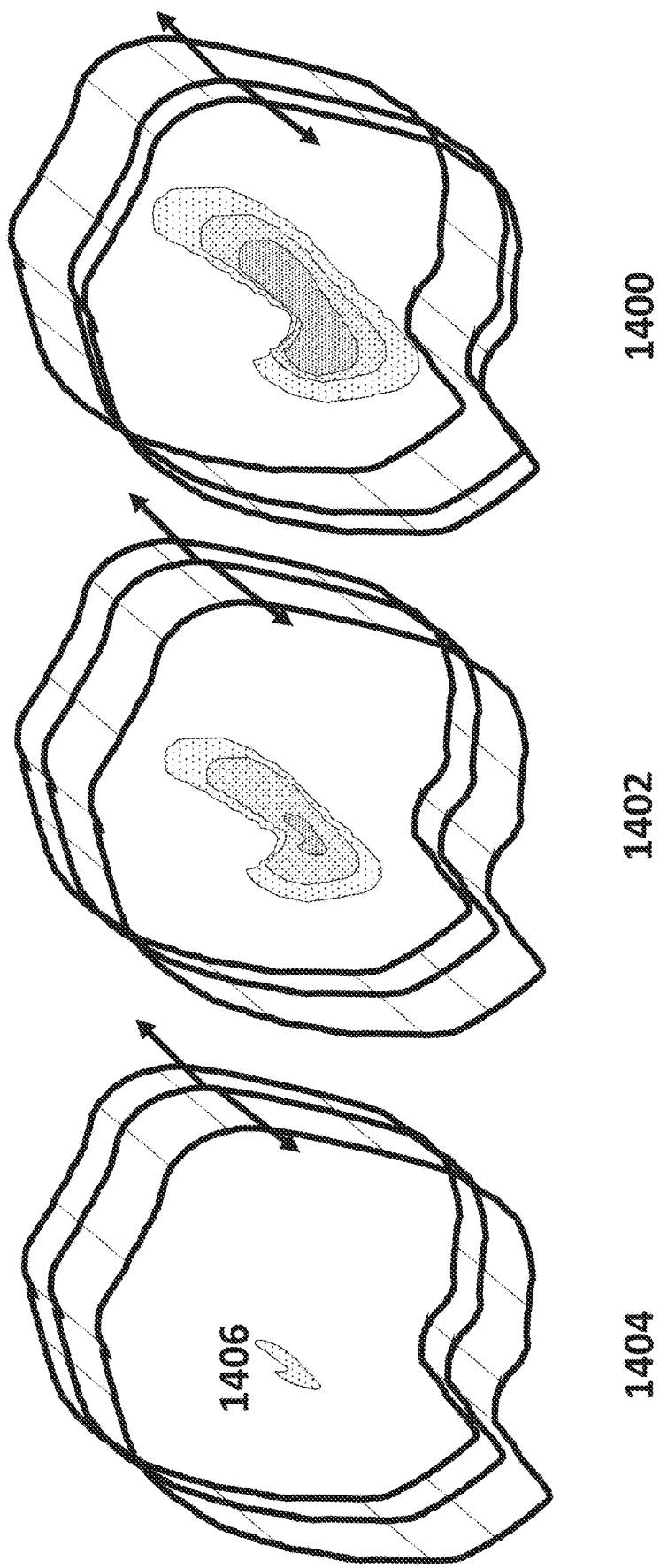
FIG. 14 is another schematic representation of an exemplary visualization technique, where several slides are shown concurrently.

Referring now to FIG. 14, showing a schematic representation of another exemplary visualization technique. In the Figure, it is shown an alternative method of visualization, where the color-coding is shown for the specific selected manifold of interest within the wireframe. In this example, three displays are provided concurrently. The display of the inner manifold 1400, the display of the intermediate manifold 1402 and the display of the outer manifold 1404. In display 1404, it is shown that the lesion actually reached the back wall of the heart at some lower level of intensity 1406.

Figure 15:
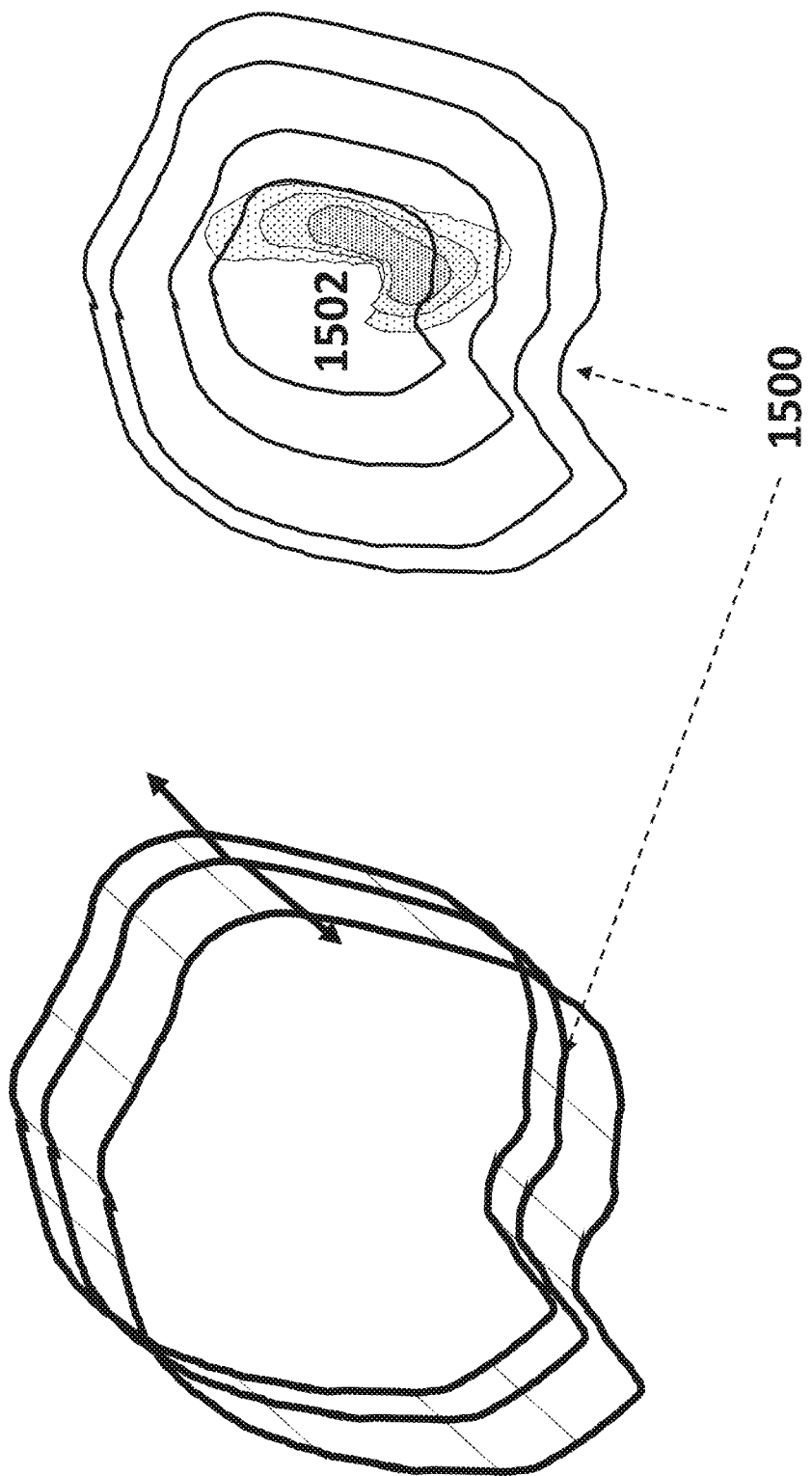
FIG. 15 is another schematic representation of an exemplary visualization technique, where the 3D characteristics of a selected manifold is provided with contour display.
Figure 16:
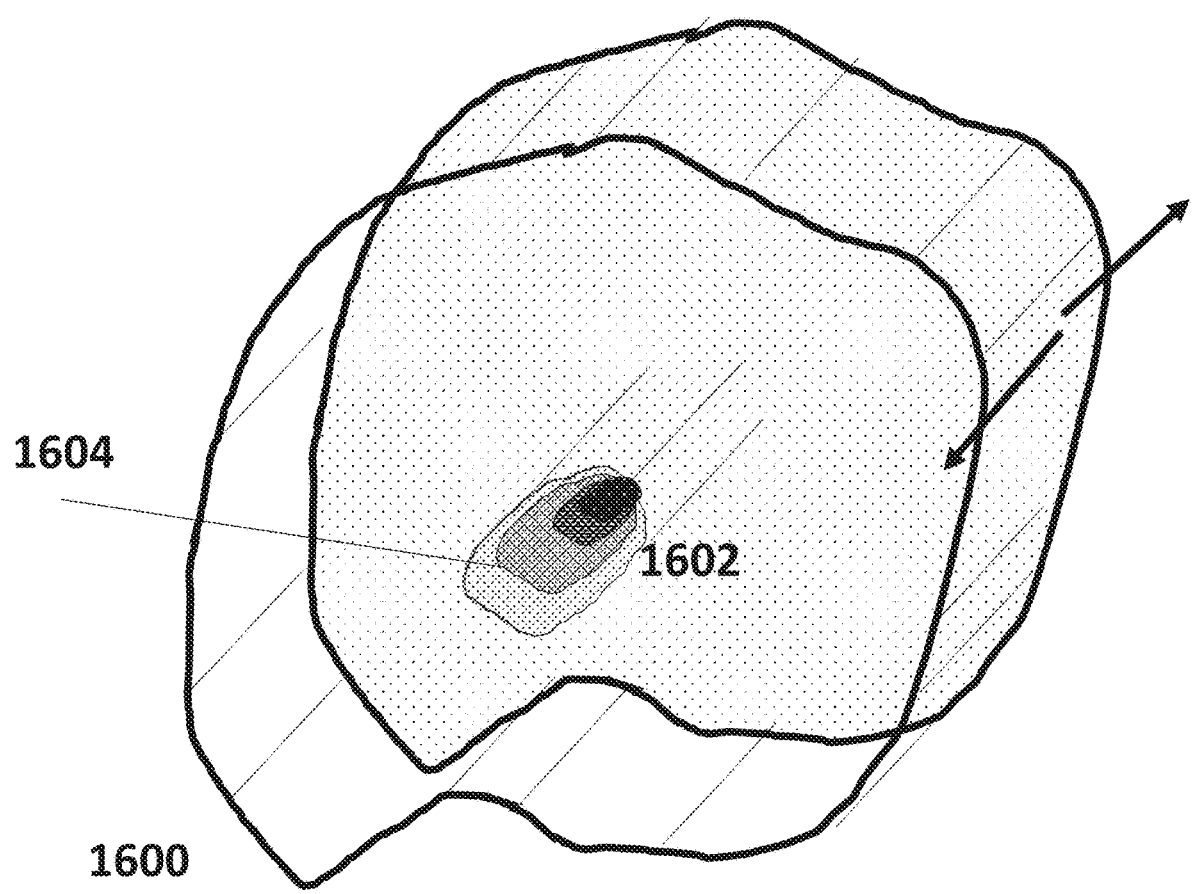
FIG. 16 is another schematic representation of an exemplary visualization technique, displaying a wire-frame of the heart as well as a wireframe of the lesion.

Referring now to FIG. 15, showing a schematic representation of another exemplary visualization technique. In the Figure, it is shown an alternative method where the 3D characteristic of the selected manifold 1500 is provided with contour display. The lesion intensity 1502 is shown as color code Referring now to FIG. 16, showing a schematic representation of another exemplary visualization technique. In the Figure, it is shown an alternative method where a single display shows the wireframe of the heart wall 1600 as well as the wireframe of the lesion 1602. By selecting the depth, the specific contour of the lesion is highlighted, as demonstrated by a wide contour line 217

Figure 17:
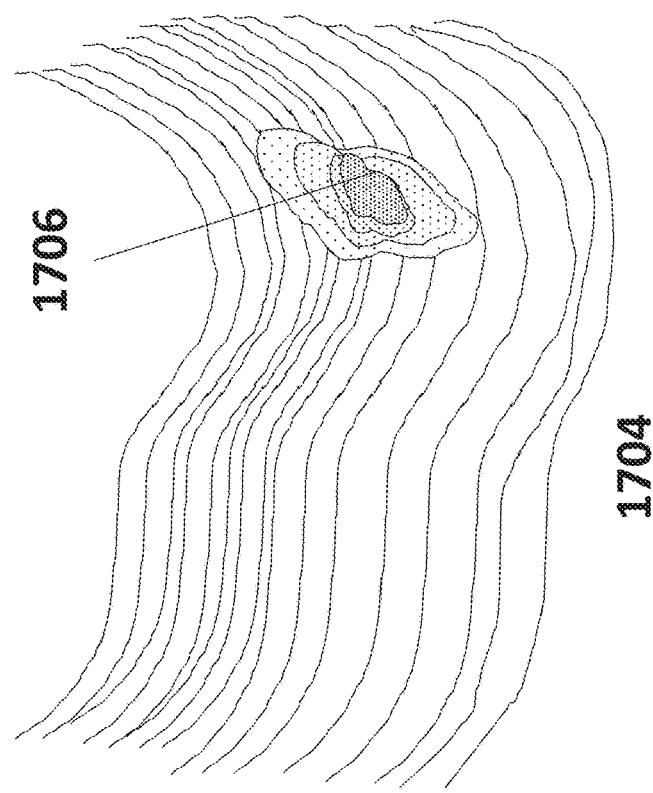
FIG. 17 is another schematic representation of an exemplary visualization technique, where the heart wall is visualized as rotatable dense wireframes.
Figure 17:
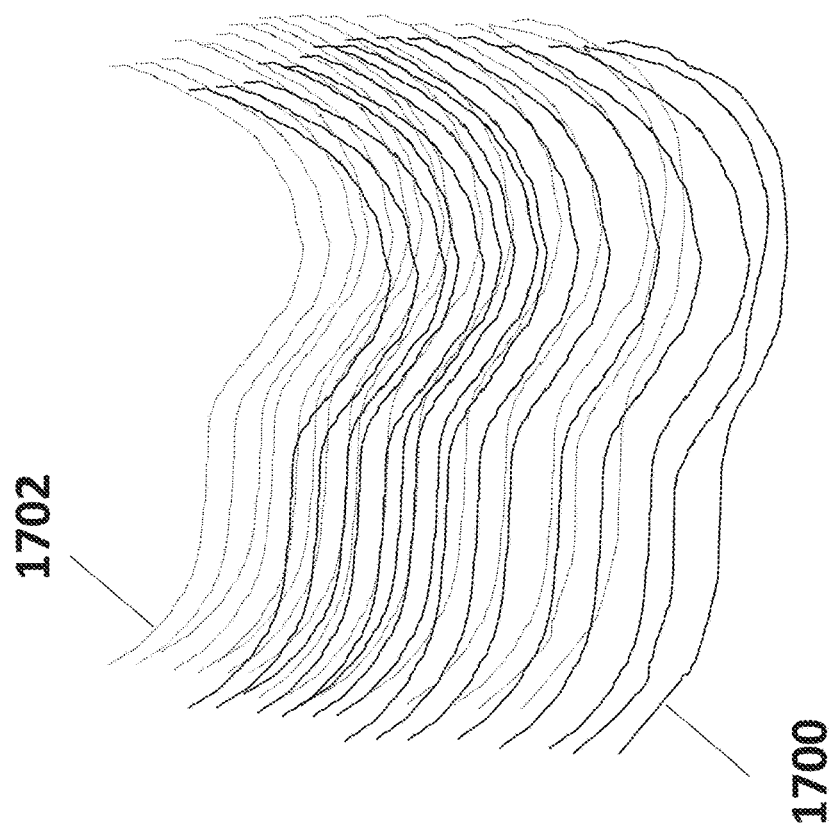

Referring now to FIG. 17, showing a schematic representation of another exemplary visualization technique. In the Figure, it is shown an alternative method where the heart wall is depicted with dense wireframes, in this case of the bottom part of the right and left ventricles. The external part of the wall is shown with thick wires 1700 while the inner part of the wall is provided with thin lines 1702. In some embodiments, the user may turn and rotate the image. In this example, the heart wall is shown from the distal part. The selected depth is shown in the right hand side of the visualization display 1704. The lesion is given in transparent color code 1706.

Cardiac Ablation

Without be limited by a particular explanation or theory, the heart may be conceptualized as a muscle organ, performing as a pump driving the blood through the veins and arteries to lungs and/or other organs in the body. The pumping action is performed by repetitive contractions of the heart, where each contraction propagates through the heart to drive the blood through the proper valves in the right direction. Contraction may be driven by an electric signal generated by pacing cells in the sinoatrial node. In a healthy state, the electric signal propagates through the heart cells by a system of action potentials. For example, a cell pulses electrically when its electric potential rises above a certain threshold, driving its neighboring cells to pulse and so on. After pulsing, the cell is drained, and its potential builds up again slowly over time. The cell will be inhibited from pulsing again until its potential builds up to a sufficient level. In this way the signal may propagate between the cells in one direction, and/or the muscle contracts with it.

One kind of heart disease is cardiac arrhythmia. This is a condition where the heartbeat is irregular—too fast, too slow, includes multiple pathways, includes reentry circuits, ectopic sites, scar tissue and/or other sources of irregular signal conduction.

An ablation process may be used to destroy heart cells, which are not functioning well, are ectopic, and/or are located in a region which is assumed to enable blockage of an arrhythmia. Forming lesions stops electric signals from passing through the poorly function cells—forcing the signal to propagate over an alternative path. The alternative path may maintain more regular propagation pathways and/or heart beats. The process may entail intentional and/or non-intentional damage to tissue. For example, the means of inflicting the damage to cause the lesion are sometimes not precise. For example, the effect may not be complete, and/or the effective depth of treatment may be imprecise. In some cases, it may not be known whether only a part of the target tissue was affected or all, and/or other non-target tissue was affected as well. The exact state of the target cells may be unknown. For example, it may be unknown whether a generated condition is temporary, for example an edema and/or an ischemia. For example, may not be known whether permanent cell death was obtained at all target locations of the tissue. Therefore, ablation procedures may failure and/or arrhythmia may reoccur some time after ablation. In some cases, several attempts and/or interventions may be performed to achieve a desired effect.

In some embodiments, during an ablation process the operator is interested in knowing which tissue was scarred, and to what extent. In some embodiments, this knowledge is used to avoid unnecessary collateral damage to healthy cells (for example by continuing ablation after a desired effect was already achieved) and/or to verify that targeted cells are fully destroyed. In some embodiments, verifying full destruction of target cells helps avoids resuscitation of the target cells after the procedure. In some embodiments, avoiding resuscitation of target cells may result in avoiding repeating a treatment to achieve full inhibition. In some embodiments, during ablation, the depth of ablation is supervised by following the depth of the changes in tissue function in the region of the ablation. In some embodiments, the extent of the ablation is estimated by comparing the functioning of the newly ablated tissue to tissue whose extent of ablation is known.

Figure 18:
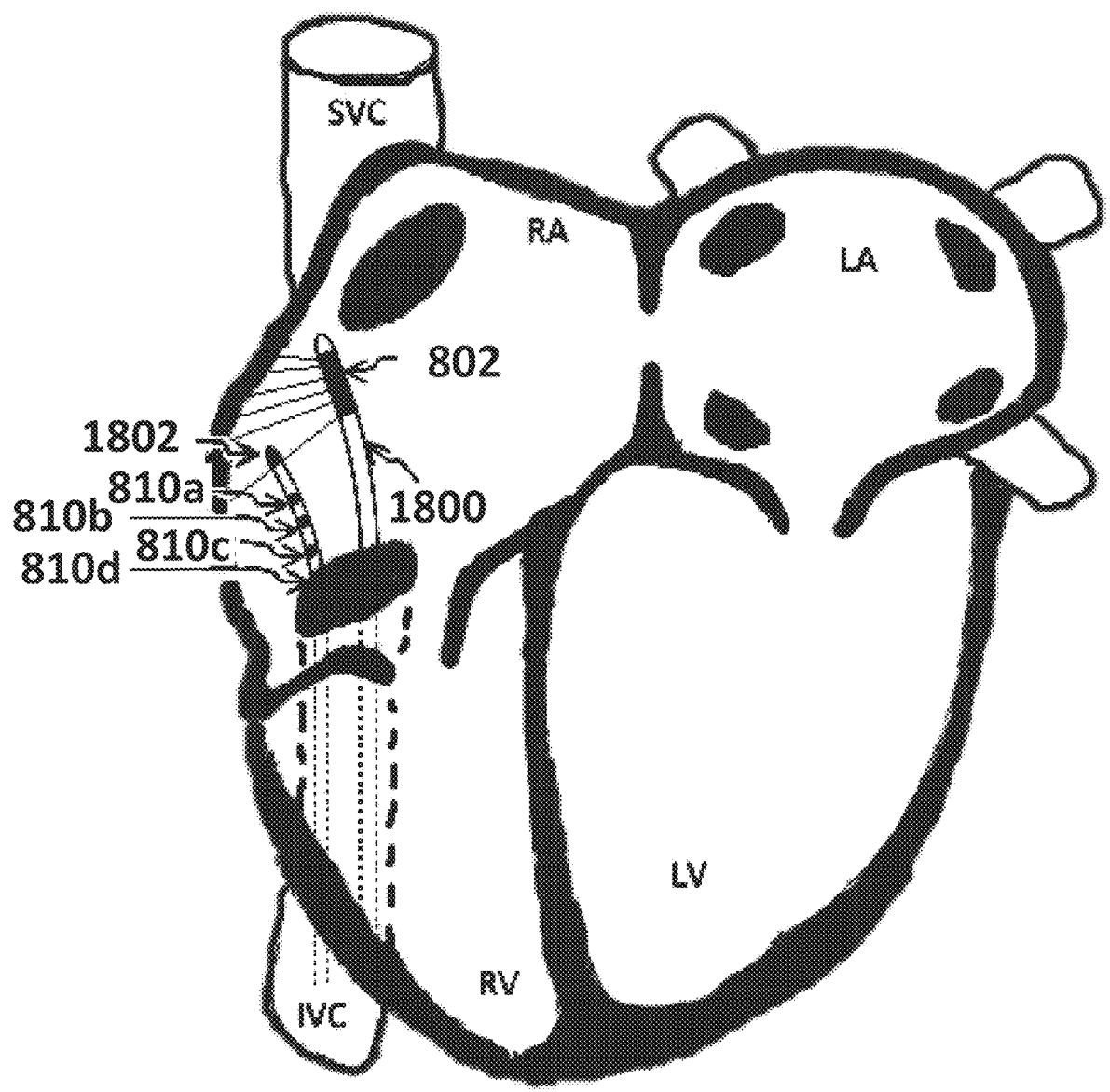
FIG. 18 is a schematic representation of an ablation procedure, including a heart and its internal structure, with catheter devices entering from the inferior vena cava into the right atrium.

Referring now to FIG. 18, showing a schematic representation of an ablation procedure, according to some embodiments of the present invention. In some embodiments, the ultrasound transducer 802 and/or the sensing electrodes 810*a-d* are intra-corporeal, for example as part of catheters. In some embodiments, the procedure is used to treat Atrial Flutter. For example, catheters enter the Right Atrium (RA) through the IVC (Inferior Vena Cava). In some embodiments, the ultrasound probe catheter 1800, optionally carries an ultrasound transducer 802. In some embodiments, the ablation catheter 1802, optionally carries the electrodes 810*a-d* and/or the ablation tip. In some embodiments, electrical properties of the tissue are measured by the system using, for example, the Acousto-Electric effect. In some embodiments, processing and/or analysis of measured values, optionally guides the ablation procedure. In some embodiments, data is arranged into 2D or 3D maps of electrical activity. Optionally the maps are used to determine positioning and/or navigation and/or to asses lesion production, for example by measures relevant to the lesion assessment stage of the procedure.

In some embodiments, the system is used to treat a case of Ventricle Tachycardia (VT). For example, the catheters may enter the Right Ventricle (RV) and/or to the Left Ventricle (LV) (for example towards the free wall, septum or other region) through the IVC, SVC (with passage through the valves and/or atrial septum) and/or through the aorta. In another example, the ultrasound unit is positioned in the esophagus (for example similarly to or using a trans-esophageal ultrasound). In another example, the ultrasound unit is extracorporeal. In some embodiments, the ultrasound catheter is positioned in one chamber, and used to observe and/or guide a procedure conducted in another chamber. In some embodiments of the present invention, the system is used to treat a case of Atrial Fibrillation (AF). For example, the catheters may enter the Left Atrium (LA) through the IVC, RA and the Interatrial Septum.

In some embodiments of the present invention, the system is used to treat a case of Ventricular arrhythmia (e.g. VT). For example, the catheters may enter the Left Atrium (LA) through the IVC, RA and/or the Interatrial Septum and through the mitral valve.

Exemplary Assessment of Effectiveness of Ablation and Assessment of Deepness of Ablation in the Tissue As mentioned above, during ablation procedures, it is important to know how deep into the tissue the ablation has arrived and how effective was the ablation treatment.

Prior art technologies measures conductance of tissues by attaching electrodes to the surface of the tissues. Sometimes, measurements received from one electrode (having a single value—e.g. impedance) regarding the property of a "bulk" of tissue, apparently suffer heavily from:

(a) Unknown total volume that participated in the measurement;
(b) Unknown current paths within the volume, so the contribution of different "small voxels" and different depths is unpredictable;
(c) Uncontrolled orientation, contact or force applied to the tissue by the electrodes;
(d) A blend of matter, including muscle which is viable/hibernated/edema/blood/blood vessels/fat/fibrous tissue, tissue and fluids beyond the muscle, and more.

Therefore, while the existence of a phenomena (e.g. conductance) may potentially be clearly associated (biologically and physiologically) with tissue state—the ability to measure with poor resolution from 2 points, which are superficial to the muscle, is very limited and is apparently not useful in determining clear and robust thresholds.

In some embodiments, assessment of ablation is performed not only on the surface of the tissue, but also deep into the tissue. In some embodiments, the deepness of the ablation procedure into the tissue is monitored by assessing the electrical activity of the tissue at a specific depth, optionally compared to the electrical activity of a tissue near the specific tissue that is being assessed. In some embodiments, the effectiveness of the ablation procedure is monitored by assessing the electrical activity of the tissue at a specific depth.

Rationale of the Electrical Activity in the Heart at Different States

Without be limited by a particular explanation or theory, the ventricular cardiomyocyte membrane potential is about −90 mV at rest, which is close to the potassium reversal potential. When an action potential is generated, the membrane potential rises above this level in four distinct phases. The beginning of the action potential, phase 0, specialized membrane proteins (voltage-gated sodium channels) in the cell membrane selectively allow sodium ions to enter the cell. This causes the membrane potential to rise at a rate of about 300 V/s. As the membrane voltage rises (to about 40 mV) sodium channels close due to a process called inactivation. The $Na^+$ channel opening is followed by inactivation. $Na^+$ inactivation comes with slowly activating $Ca^{2+}$ channels at the same time as a few fast $K^+$ channels open. There is a balance between the outward flow of $K^+$ and the inward flow of $Ca^{2+}$ causing a plateau of length in variables. The delayed opening of more $Ca^{2+}$-activated $K^+$ channels, which are activated by build-up of $Ca^{2+}$ in the sarcoplasm, while the $Ca^{2+}$ channels close, ends the plateau. This leads to repolarization. The depolarization of the membrane allows calcium channels to open as well. As sodium channels close calcium provides current to maintain the potential around 20 mV. The plateau lasts on the order of 100 ms. At the time that calcium channels are getting activated, channels that mediate the transient outward potassium current open as well. This outward potassium current causes a small dip in membrane potential shortly after depolarization. This current is observed in human and dog action potentials, but not in guinea pig action potentials. Repolarization is accomplished by channels that open slowly and are mostly activated at the end of the action potential (slow delayed-rectifier channels) and channels that open quickly but are inactivated until the end of the action potential (rapid delayed rectifier channels). Fast delayed rectifier channels open quickly but are shut by inactivation at high membrane potentials. As the membrane voltage begins to drop the channels recover from inactivation and carry current.

As can be understood from the explanation above, the heart tissue comprises a variety of ions that constantly move in and out the cell membrane. It can be noted that the polarization and membrane permeability (ion conductance), both change dramatically during the cardiac cycle. Apparently, there are great differences in ion concentrations between compartments (outside the cell, inside the cell, and sometime specific compartments within the cells), which vary per ion type. There are 1 or 2 orders of magnitude on permeability of channels to ions between rest mode and active mode, there are fast ion currents that occur at the activation of the cells, and there are mechanical changes (shortening, stiffening) from the rest mode to the active mode (systole).

Figure 19:
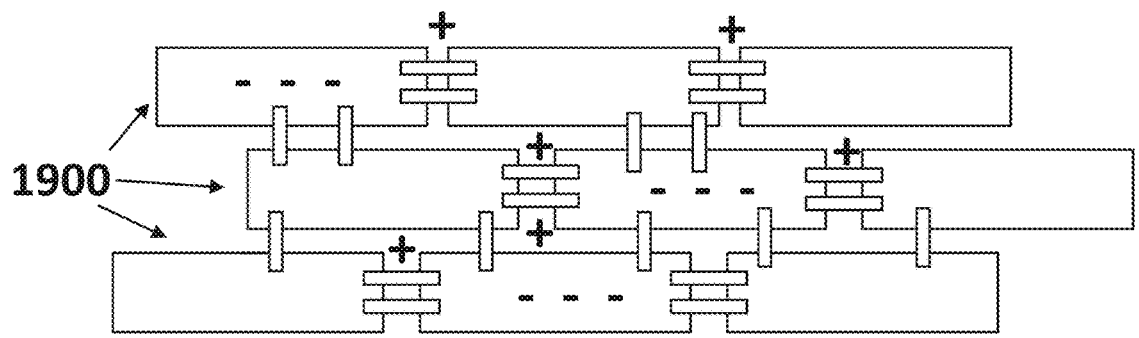
FIG. 19 is a schematic of heart cells at three degrees of ablation damage, and how electric charges and dipoles are arranged inside and between the cells.
Figure 19:
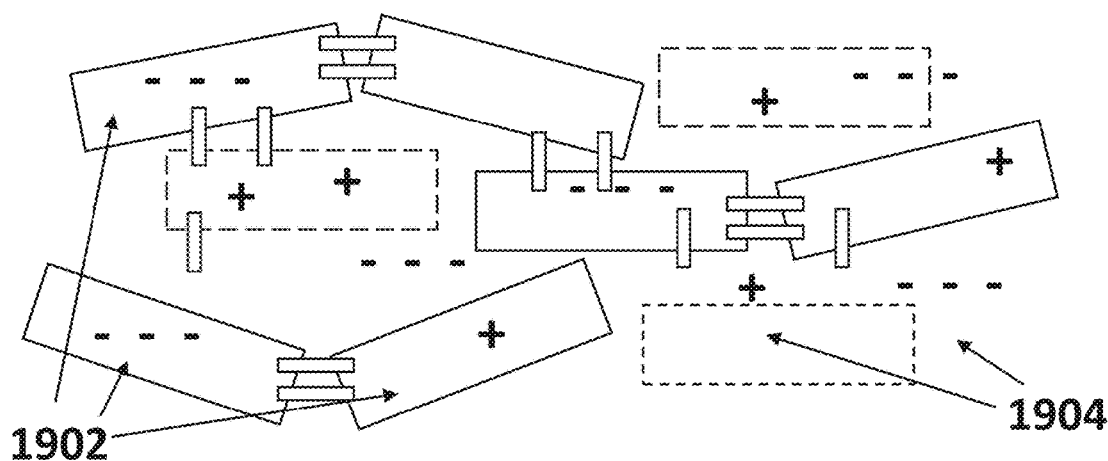
Figure 19:
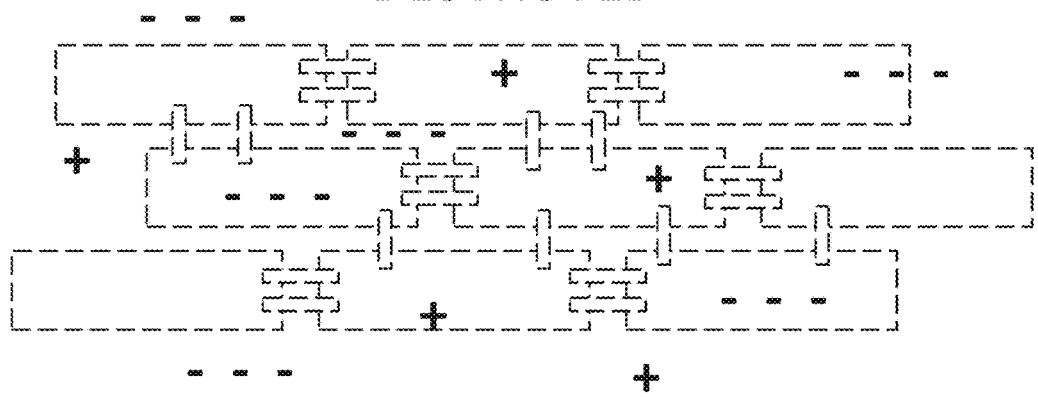

Referring now to FIG. 19, showing a schematic representation of the principle of ablation assessment. Normal (upper side of the figure) viable cardiac muscle tissue 1900 has pulsation (and alternations) in its cycle. Within a cardiac cycle there are changes in mechanical and electrical properties: during the action potential and the systole the tissue becomes shorter, stiffer, membrane conductance (permeability) of ions increases dramatically. The tissue structure is constructed of polarized cells, with alternating changes to its polarity (from a lower range from about −80 mv to about −90 mV in rest mode, to a higher range from about 0 mV to about +40 mV in the peak, but mostly about 0 mv in the depolarized, active mode). It is hypothesized that the conductance varies between low conductance (in rest mode) to higher conductance (during action potential), and polarity alternates between highly polarized to none or reversed polarization (during action potential).

During partial damage (middle part of the figure), the tissue may enter a "hibernation" state (e.g. due to cooling) or in cases of edema (due to moderate and recoverable tissue damage, for example in cases of incomplete ablation process), some of the structure is maintained 1902. It is believed that, while there may be fluids accumulation and changes in concentrations in the inter and intra cellular spaces 1904, membrane remains mostly complete and cells can recover after a while. In this condition, cells and arrhythmia may become apparent after a recovery period (could be minutes, hours, days, weeks and even months). During the hibernation or edema conditions, there is no or minimal pulsation and alternations in polarity and in conductance. However, some polarity is maintained as the membrane is not completely destroyed. It is hypothesized that the conductance of the tissue in this state is medium, being higher than in the resting, due to changes in concentrations and accumulation of fluids. The polarization of cells remains, though not (or minimally) pulsatile, and probably the polarization is at a lower and non-homogeneous degree than in normal tissue at rest mode.

When tissue is completely destroyed (lower part of figure) in a non-recoverable manner, it is believed that such destruction includes protein destruction or denaturation as well as cell membrane destruction that does not enable proper separation between intracellular space and extracellular space. It is hypothesized that conductance increases materially to a high level, as membrane do not resist ions transport; there is no polarization at this state.

Exemplary Ablation Assessment Parameters

In some embodiments, bio-impedance approach is used to relative changes in states (normal, partially damage, destroyed) locally, as there is gradual increase in conductance during the progress along the stages. In some embodiments, the analysis is performed in a gated manner, to overcome tissue motion. In some embodiments, the analysis is performed with high-resolution voxel separating along the depth, and in the x-y plane, to avoid blurring of the measurement and assessment of tissue state. In some embodiments, the pulsatile/alternation property (e.g. measuring every few milliseconds, e.g. every 1, 3, 5, 10, 20, 50 milliseconds) is used. Optionally, while compensating for motion, to discriminate normal (functioning) viable tissue segments (voxels) from hibernating, edema, non-functioning or dead tissue. In some embodiments, the pulsatile/alternation property for impedance and/or conductance evaluation (e.g., when current is induced) is used also for measurements of electrical fluctuations due to polarity changes. In some embodiments, the use of the acoustoelectric effect taking into account locality of measurements thus providing high resolution. In some embodiments, the use of acoustoelectric effect has three properties (polarization, ion conductance and mechanical properties (e.g. elasticity)) that are measured simultaneously or sequentially. In some embodiments, with no induced current, a substantially greater signal is produced, as vibrating object is polarized (contrary to non-polarized), therefore discriminating dead versus non-dead tissue. In some embodiments, with induced current, information about ion conductance in the object is achieved, which reacts to the changes between the above-mentioned tissue states. In some embodiments, in both modes (induced and non-induced current), the effect depends on the mechanical properties of the target (e.g. the elasticity of the object), therefore it is sensitive to a variety of conditions, like: fluid volume (e.g. in blood), structured tissue in edema, non-structured object, stiff target (e.g. in muscle contracted state), softer structure (e.g. in muscle relaxed state). In some embodiments, in both modes, higher depth (and X-Y) resolution provides better discrimination among tissue states by reducing blurring due to non-homogenous "bulk" of tissue.

In some embodiments, the system takes into account the changes in tissue ability to maintain polarity, both instantaneously (alternations within the cardiac cycles) and over several seconds and/or minutes of procedure. In some embodiments, this enables detection of polarized vs non-polarized tissue, as vibration of an object with homogenous ion deposition within the volume comprises less pronounced radiation of electrical potential (electro-acoustic effect) than vibration of an object with dipoles. In some embodiments, the fast (alternating within cardiac cycle) changes in conductance and in radiated voltage (as measured in the frequency of the acoustic vibration) provides information about the tissue pulsatile properties, about the membrane ability to block conductance, and about the tissue polarization.

In some embodiments, the combination of some or all the above provide multiple properties that provide:

Real time activation map, for example measuring changes with time resolution of 1, 2, 5, 10, 20, 50 milliseconds or longer, for example in 2D and/or in 3D (e.g. in different depths of the tissue); and/or Tissue characterization and discrimination between tissue types and tissue states, for example measuring changes with time resolution of 0.1, 0.5, 1, 2, 5, 10, 20, 30, 60 seconds or longer, for example in 2D and/or 3D (e.g. in different depths of the tissue).

In some embodiments, the properties are provided superficially (as a surface/manifold representation for one or more of: endocardium, epicardium, a layer between them and/or superficial layer and/or one or more flat or non-flat 2D maps).

In some embodiments, the properties are provided in multiple layers of depth, as a 2D or 3D representation of processed score that takes into account information from one or more depths and/or from one or more properties.

In some embodiments, the properties are provided with motion compensation (for breathing, and/or systole-diastole cardiac motion) and/or with partial motion compensation, and/or with gated display that analyzes and/or provides one or more different maps along the cardiac cycle.

Exemplary Methods

Figure 20:
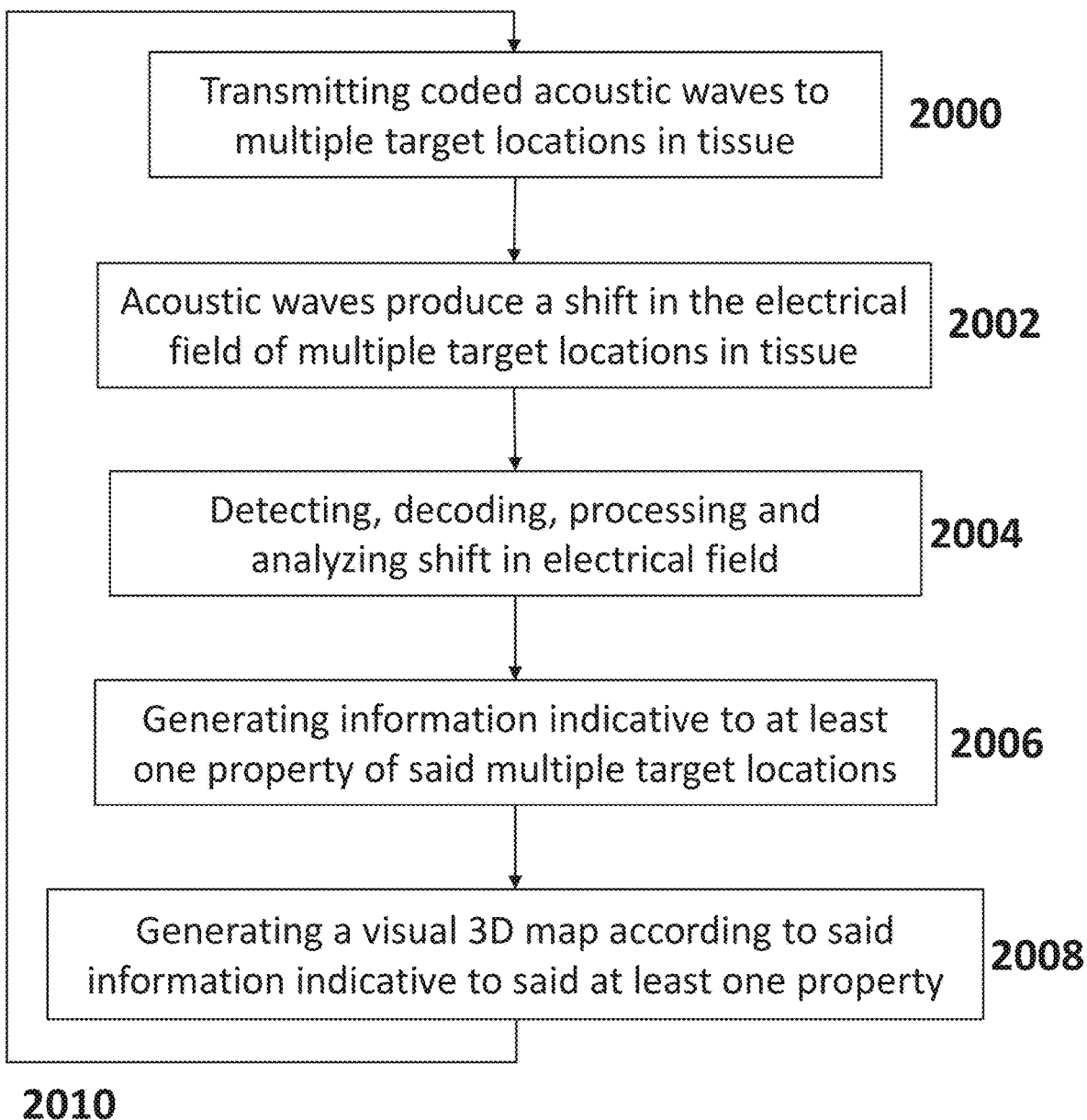
FIG. 20 is a schematic flowchart of a method of how the system works using exemplary coded acoustic waves to generate a tridimensional map of at least one property of the target tissue, according to some embodiments of the present invention.

Referring now to FIG. 20, showing a schematic flowchart of a method of how the system works using exemplary coded acoustic waves to generate a tridimensional map of at least one property of the target tissue, according to some embodiments of the present invention. In some embodiments, the systems begins by transmitting a plurality of coded acoustic waves to multiple target locations in tissue 2000, each coded acoustic wave is transmitted to a specific area in the target location. In some embodiments, the acoustic waves produce a shift in the electrical field of the multiple target locations in the tissue 2002. In some embodiments, the system continues by detecting, decoding, processing and analyzing the shift in electrical field 2004, according to chosen parameters, for example one or more of the specific locations or the depth in the tissue. In some embodiments, the system continues by generating information indicative to at least one property of said multiple target locations 2006, said property is derived from the behavior of the shift in the electrical field of the target location in the tissue. In some embodiments, system continues by generating a visual 3D map according to said information indicative to said at least one property 2008. In some embodiments, system continues by repeating the process 2010 in order to acquire an updated map of the electrical behavior in the target location in the tissue.

Figure 21:
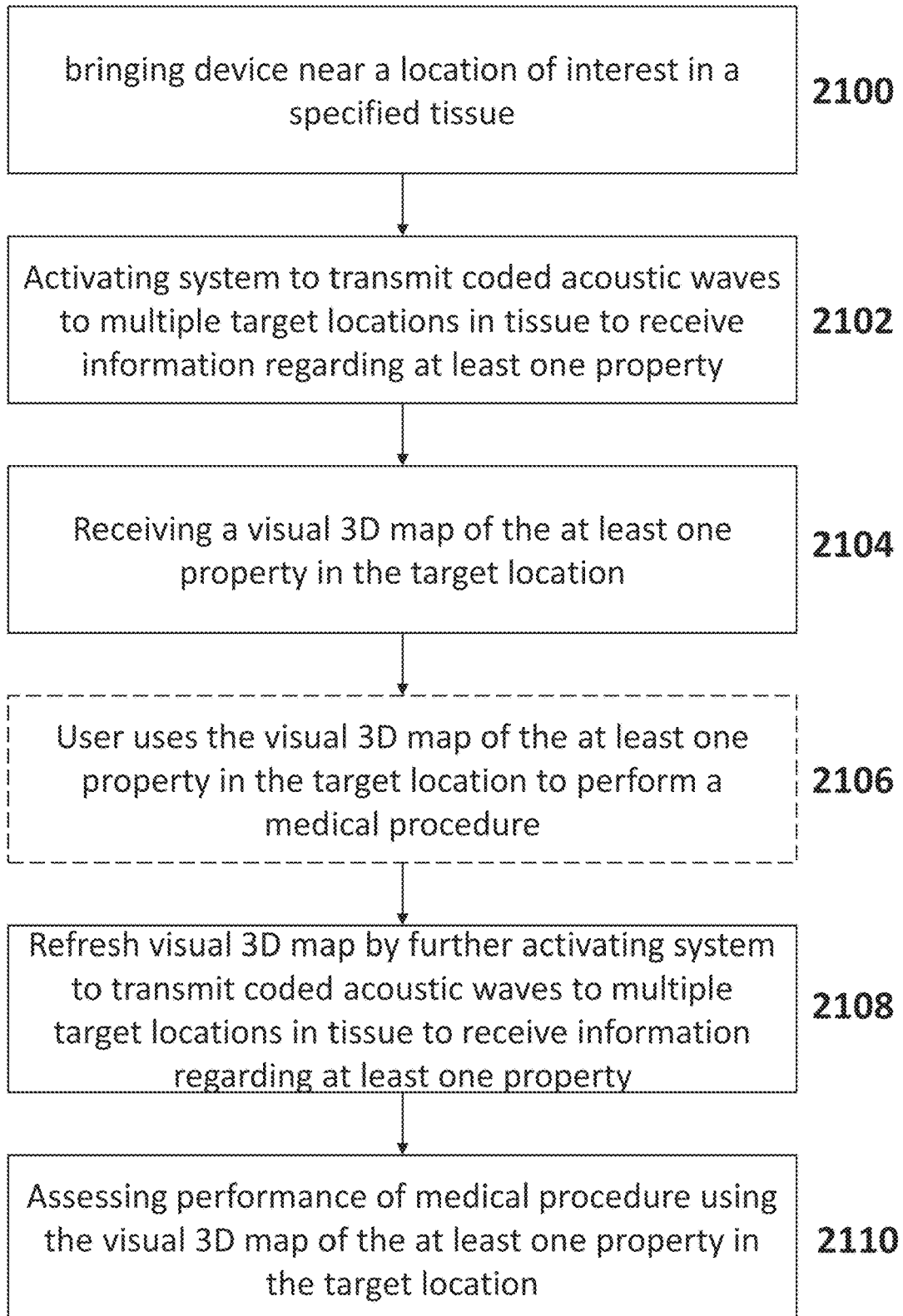
FIG. 21 is a schematic flowchart of a method of how the user uses the system to generate a visual 3D map of at least one property of a target location in a tissue, using exemplary coded acoustic waves, according to some embodiments of the present invention.

Referring now to FIG. 21, showing a schematic flowchart of a method of how the user uses the system to generate a visual 3D map of at least one property of a target location in a tissue, using exemplary coded acoustic waves, according to some embodiments of the present invention. In some embodiments, the user begins by bringing device near a location of interest in a specified tissue 2100. In some embodiments, the user continues by activating the system to transmit coded acoustic waves to multiple target locations in the target tissue to receive information regarding at least one property of said target location 2102. In some embodiments, the user receives a visual 3D map of the target location showing and according the at least one property 2104. In some embodiments, the user uses the visual 3D map of the at least one property in the target location to perform a medical procedure (e.g. cardiac ablation) 2106. In some embodiments, the user refreshes the visual 3D map by further activating system to transmit coded acoustic waves to multiple target locations in the tissue to receive information regarding said at least one property 2108. In some embodiments, the user can assess the performance of medical procedure using the visual 3D map of the at least one property in the target location 2110, for example, there is not shifting in the electrical field; therefore it can be assumed that the cells are dead.

As used herein with reference to quantity or value, the term "about" means "within ±20% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

What is claimed is:

1. A system for tissue characterization using an acousto-electric effect comprising:
   a. one or more acoustic waveform generators for generating plurality of waveforms;
   b. at least one waveform generation controller;
   c. at least one set of electrodes;
   d. at least one electric signal amplification circuitry connectable to at least one of said at least one set of electrodes to generate an amplified signal; and
   e. at least one signal processing unit comprising instructions for analyzing received reflected signals from said amplified signals and to generate information indicative to at least one property of multiple locations within a target tissue taking into account said acousto-electric effect;
   wherein said at least one waveform generation controller comprises instructions for:
   i. generating said plurality of waveforms according to at least one parameter, each of said plurality of waveforms comprising a coded sequence which is different from other coded sequences comprised in other generated waveforms; said plurality of different coded sequences being used in said analyzing by said at least one signal processing unit; said at least one parameter being a low maximal absolute value of cross correlation between said sequences thereby providing a maximal signal to interference ratio between generated waveforms; and
   ii. transmitting said generated plurality of waveforms;
   wherein said analyzing comprises separating contributions from each of said received signals based on said difference in said coding sequence of each of said waveforms.

2. The system according to claim 1, wherein each of said coded sequences comprise a single narrow high peak auto-correlation at certain timing during a transmission of said coded sequence with low auto-correlation when not at said certain timing.

3. The system according to claim 1, wherein different sequences are selected for different acoustic waveform generators when more than one acoustic waveform generators are used.

4. The system according to claim 1, wherein at least one of said multiple locations has no direct contact with any electrode.

5. The system according to claim 1, wherein said properties of said multiple locations are obtained within up to 10 milliseconds of generated waveforms per location on average.

6. The system according to claim 1, wherein said information indicative to at least one property of multiple locations within a target tissue is presented as a three-dimensional map.

7. The system according to claim 6, wherein said three-dimensional map indicates an activation sequence of said tissue.

8. The system according to claim 1, wherein said at least one property is selected from the group consisting of:
   a. tissue viability state;
   b. effectiveness of ablation procedure;
   c. effective depth of an ablation;
   d. whether an ablation was trans-mural;
   e. ablation damage to surrounding non-target tissue;
   f. tissue electrical activity state;
   g. tissue electrical action potential;
   h. tissue electrical propagation velocity;
   i. tissue electrical propagation direction;
   j. tissue electrical conductance;
   k. tissue electrical impedance.

9. The system according to claim 1, wherein said properties of at least one of said multiple locations comprise one or more of the conditions selected from group consisting of normal, alive, dead, scar, fibrotic, edema, alive and functioning, alive and not functioning.

10. The system according to claim 1, wherein said tissue is a cardiac tissue.

11. A method of tissue characterization using an acousto-electric effect comprising:
   a. providing at least one waveform generation controller for generating a plurality of acoustic waveforms;
   b. irradiating said tissue with said plurality of acoustic waveforms;
   c. detecting an acoustoelectric voltage signal by means of at least one set of electrodes;
   d. processing and analyzing said acoustoelectric voltage signal by at least one signal processing unit;
   e. generating information indicative to at least one property of multiple locations within said tissue taking into account said acousto-electric effect;
   wherein said at least one waveform generation controller comprises instructions for:
   i. generating said plurality of waveforms according to at least one parameter, each of said plurality of waveforms comprising a coded sequence which is different from other coded sequences comprised in other generated waveforms; said plurality of different sequences being used in said analyzing by said at least one signal processing unit; said at least one parameter being a low maximal absolute value of cross correlation between said sequences thereby providing a maximal signal to interference ratio between generated waveforms; and ii. transmitting said generated plurality of waveforms;

wherein said analyzing comprises separating contributions from each of said received signals based on said difference in said coding sequence of each of said waveforms.

12. The method according to claim 11, wherein each of said coded sequences comprises a single narrow high peak auto-correlation at certain timing during a transmission of said coded sequence with low auto-correlation when not at said certain timing.

13. The method according to claim 11, wherein different sequences are selected for different acoustic waveform generators when more than one acoustic waveform generators are used.

14. The method according to claim 11, wherein said generating information indicative to at least one property comprises generating information indicative to tissue viability state.

15. The method according to claim 11, wherein said generating information comprises generating said multiple locations as a three-dimensional map; and said three-dimensional map indicates an activation sequence of said tissue.

16. The method according to claim 15, further comprising superimposing and aligning in three dimensions said three-dimensional map with an anatomical map of the tissue.

17. The system according to claim 1, wherein said at least one signal processing unit is further configured for analyzing said amplified signal and to further generate information indicative to at least one property of multiple locations within at least one volume.

18. The system according to claim 1, wherein said plurality of waveforms include at least one random coded sequence.

19. The system according to claim 1, wherein said plurality of waveforms includes at least one barker sequence.

20. The system according to claim 1, wherein different coded sequences are selected for different times of generated waveforms when more than one acoustic waveform generators are used.

21. The system according to claim 1, wherein at least one of said plurality of waveforms is transmitted in a different direction from another one of said plurality of waveforms.

22. The system according to claim 1, wherein said analyzing comprises analyzing multiple volumes simultaneously.

* * * * *